United States Patent [19]
Arnold, Jr. et al.

[11] Patent Number: 5,837,856
[45] Date of Patent: Nov. 17, 1998

[54] CHIRALLY ENRICHED SYNTHETIC PHOSPHONATE OLIGOMERS

[75] Inventors: Lyle J. Arnold, Jr., Poway; Mark A. Reynolds, San Diego; Timothy A. Riley, Nipomo; David A. Schwartz, Encinitas, all of Calif.

[73] Assignee: Genta, Incorporated, San Diego, Calif.

[21] Appl. No.: 814,053

[22] Filed: Mar. 6, 1997

Related U.S. Application Data

[63] Continuation of Ser. No. 154,013, Nov. 16, 1993, abandoned.

[51] Int. Cl.[6] .................................................. C07H 21/04
[52] U.S. Cl. ............................ 536/24.5; 435/6; 536/25.3
[58] Field of Search ............................... 435/6; 536/24.5, 536/25.3, 25.33, 26.7, 26.8

[56] References Cited

U.S. PATENT DOCUMENTS 5,212,295  5/1993  Cook ...................................... 536/26.7

FOREIGN PATENT DOCUMENTS

WO92/02532  2/1992  WIPO ............................ C07H 17/00

*Primary Examiner*—Scott W. Houtteman
*Attorney, Agent, or Firm*—Knobbe, Martens, Olson & Bear, LLP

[57] ABSTRACT

Oligomers having phosphonate internucleosidyl linkages which are enriched for phosphonate linkages of a preselected chirality which hybridize to an RNA target sequence and methods for their preparation are provided.

22 Claims, 3 Drawing Sheets

B=A,C,G and T

CHIRALLY ENRICHED SYNTHETIC PHOSPHONATE OLIGOMERS

This application is a continuation of application Ser. No. 08/154,013, filed Nov. 16, 1993, now abandoned.

BACKGROUND AND INTRODUCTION OF THE INVENTION

The present invention is directed to chirally enriched synthetic Oligomers which are chirally enriched for phosphonate linkages of a preselected chirality and to methods for their synthesis. In particular, we have found that chirally enriched Oligomers enriched for Rp methylphosphonate internucleosidyl linkages have enhanced binding affinities for RNA. The chirally enriched Oligomers of the present invention may be enriched for methylphosphonate internucleosidyl linkages of Rp chirality, or for methylphosphonothioate internucleosidyl linkages of either Rp or Sp chirality.

Oligomers having naturally occurring phosphodiester internucleosidyl linkages and certain other internucleosidyl linkages do not have chiral centers at the phosphorus atom (or other atom) of the internucleosidyl linkage.

However, these phosphonate internucleosidyl linkages which include methylphosphonate and methylphosphonothioate internucleosidyl linkages are chiral at the phosphorus and have either Rp or Sp chirality depending on the relative orientation of the hydrogen or alkyl group. Thus, Oligomers having such internucleosidyl linkages may theoretically have $2^n$ different diastereomeric forms for a particular Oligomer where n is the total number of phosphonate and internucleosidyl linkages in the Oligomer sequence. For example, an 11-mer having 10 phosphonate internucleosidyl linkages theoretically would have 1,024 diastereoisomers and a 19-mer having 18 phosphonate internucleosidyl linkages theoretically would have 262,144 diastereoisomers.

The reported effects of chirality of internucleosidyl linkages on the resulting Oligomers and their biological or physical chemical behavior have been varied.

The preparation of two isomers of decathymidylate analogues having stereoregular, alternating methylphosphonate and phosphodiester backbones has been reported (Miller, et al., J. Biol. Chem. 255(20):9659–9665 (1980). Complexes between the two isomers and complementary polynucleotides were studied. The absolute configurations of the methylphosphonate groups of isomers 1 and 2 were not determined. Complexes formed by the two isomers with complementary polynucleotides were said to have different stoichiometries and thermal stabilities. Miller et al. hypothesized that in formation of a complex with a decathymidylate analog whose methylphosphonate groups were in the S-configuration the methyl group should have the least perturbational effect on solvent interactions with the complex; whereas, in contrast, complex formation with the decathymidylate analog whose methylphosphonate groups have the R-configuration would orientate the methyl group away from the base stacking region and toward the solvent and should result in "unfavorable interactions between the exposed methyl groups and the surrounding solvent."

Studies on complexes of duplex formation between a 19-mer phosphodiester oligonucleotide ($dA_{19}$, $dU_{19}$ or $dT_{19}$) and a 19-mer methylphosphonate oligonucleotide having one phosphodiester 5'-internucleosidyl linkage ($dA^*_{19}$, $dU^*_{19}$ or $dT^*_{19}$) reported that transition curves for complexes between $dA^*_{19}$ and $dT_{19}$ or $dU_{19}$ were sharp and similar to those for $dA_{19}$ and $dT_{19}$ or $dU_{19}$, whereas transition curves for duplexes of $dT^*_{19}$ or $dU^*_{19}$ and $dA_{19}$ were significantly broader, suggesting to the authors that methylphosphonate chirality had a significant influence on binding stability only when the pyrimidine strand was substituted. (Kibler-Herzog, Laura, et al., Nucleic Acids Research 18(12):3545–3555 (1990)).

A study of 2-diastereoisomeric pairs of octathymidine methylphosphonates (all Sp and SpSpSpRpSpSpSp versus all Rp and RpRpRpSpRpRpRp) compared with octathymidylic acid and a random mixture of octathymidine methylphosphonate diastereoisomers and complexes formed with penta-decadeoxyriboadenylic acid reported that configuration of the internucleosidyl methylphosphonate linkages may affect binding of $(dA)_{15}$ to the Oligomer and that the methyl in the Sp configuration decreased duplex stability. (Lesnikowski et al., Nucleic Acids Research 18(8):2109–2115 (1990).

Certain computer modeling studies reported that methylphosphonate ("MP") hybridization to a DNA target was predicted to be more stable with R-MP substitution due to favorable hydrophobic interactions whereas S-MP destabilized the double helix with less favorable hydrophobic interactions. The simulations compared antisense Oligomers having a single R-MP to S-MP substitution. (Hausheer et al., J. Am. Chem. Soc. 114:3201–3206 (1992)).

Computer modeling studies to determine the relative stability of R and S methylphosphonate Oligomers by free-energy perturbation approaches using a free-energy decomposition method were reported. The study reported that in the case of the S diastereomer the C2' and C3' sugar (5' direction) carbons and hydrogens unfavorably interacted with the methyl group, while the C5' sugar (3' direction) hydrogens destabilized the R diastereoisomer. Although the study reported the stability of the R-configuration to be favored, it was noted that under certain circumstances there may be reversals in stability of R and S diastereoisomers. (Ferguson and Kollman, Antisense Research and Development, 1:243–25 (1991)).

Studies of formation of duplexes using self-complementary DNA Oligomers having one methylphosphonate internucleosidyl linkage were reported. With the Rp duplexes, reported Tm increased when the substitution was closer to the 3'-end of the strand. With the Sp duplexes, substitution nearer the center of the strand was said to produce larger effects (e.g., greater Tm depressions) than substitution closer the either end of the duplex. In one instance of substitution between the second and third nucleoside (from the 5'-end) the Sp duplex had a higher Tm than the corresponding Rp duplex. (Bower et al., Nucleic Acids Research 15(12):4915–4930 (1987)).

In a summary of molecular modeling studies on single stranded, as well as base paired, forms of dinucleoside methylphosphcnates it was reported that neither S-MP nor R-MP seemed to significantly alter the stereochemistry of duplex structure (Latha et al., J. Biomolecular Structure Dynamics, 9(3):613–631 (1991).

In a review article summarizing certain work on antisense agents, disadvantages of poorly hybridizing racemic oligodeoxynucleoside methylphosphonates in cell free extracts were said to be more or less balanced by their proposed advantages[*/] in cell culture systems. It was noted that certain reports using a normal (deoxyribonucleoside) octamer with one methylphosphonate linkage found the Oligomer with an R bond to have a melting temperature higher than the Oligomer with an S bond. It was also noted that sequence dependence of methylphosphonate base pairing might be as important as chirality. (Wickstrom, "Antisense DNA Therapeutics Neutral Analogs and Their Stereo-chemistry" in Gene Regulation: Biology of Antisense RNA and DNA, 119 to 132 (Erickson and Izant, eds., Raven Press Ltd., New York (1992)).

*/ Greater longevity, more efficient cellular uptake and lack of charge.

Diastereoselective synthesis of dinucleoside methylphosphonates containing thymidine has been reported (Engels et al., Nucleosides & Nucleotides 10(1–3):347–350 (1991)). Diastereoselective synthesis of certain other dinucleoside! methylphosphonates using methyldichlorophosphine has been reported (Löschner et al., Tetrahedron Letters 30(41):5587–5590 (1989)).

SUMMARY OF THE INVENTION

According to one aspect, the present invention provides chirally enriched. phosphonate Oligomers and methods for their preparation. These oligomers have phosphonate internucleosidyl linkages selected from the group consisting of lower alkylphosphonate internucleosidyl linkages of 1 to 3 carbon atoms and lower alkylphosphonothioate linkages of 1 to 3 carbon atoms. Preferred phosphonate internucleosidyl linkages include methylphosphonate ("MP") and methylphosphonothioate ("MP(PS)") linkages. According to an especially preferred aspect, such oligomers are enriched for phosphonate internucleosidyl linkages of a preselected chirality. According to an especially preferred aspect, such Oligomers are enriched for the number of Rp configuration methylphosphonate internucleosidyl linkages as compared with Rp linkages in random racemic Oligomers, that is, Oligomers comprising a random racemic mix of Rp and Sp configurations at each of their methylphosphonate internucleosidyl linkages.

Among other factors, the present invention is based on our unexpected finding that synthetic methylphosphonate Oligomers described herein which are enriched in either Rp or Sp chirality display higher or lower (respectively) "net" binding affinities for their complementary RNA target sequences as compared to random racemic methylphosphonate Oligomers having the same nucleoside base sequence. By "net" is meant the arithmetic mean of the individual binding affinities for each diastereomer in an Oigomer sample. Oligomer samples that are enriched for higher binding diastereomers (that is are enriched for Rp-configuration methylphosphonate internucleosidyl linkages) show a higher "net" binding affinity. As evidence of such binding affinities, we have demonstrated that Oligomers enriched for Rp-configurations at the MP chiral centers demonstrate higher Tm's in hybridization assays with RNA target sequences than do random racemic Oligomers and whereas Oligomers enriched for Sp configurations at the MP-chiral centers demonstrate lower Tm's. We have found that these Rp enriched Oligomers demonstrate enhanced binding affinities for RNA target sequences when binding to a RNA target in either a duplex or triple helix mode. With respect to binding in a duplex mode, we have found Rp enrichment of methylphosphonate internucleosidyl linkages to give an increase in Tm of about 0.9° to 1.50° C. per internucleosidyl linkage that is in the Rp configuration as compared to a random racemic configuration. We have further found that use of 2'—O-methyl nucleosides in these oligomers results in additional increases of Tm of about 1° C. per substitution of 2'-deoxy with 2'—O-methyl nucleoside.

Reference has previously been made to the effect of chirality on the ability of methylphosphonate oligomers to hybridize to DNA targets. There are some reports in the literature that Rp-enriched oligo-dT methylphosphonates bind more tightly to DNA than their racemic counterparts. DNA targets were used in these studies rather than RNA. In view of the structural differences between helices formed using DNA and RNA targets, such data obtained with DNA targets would not suggest an application to RNA targets. Certain important physical chemical differences between DNA and RNA are discussed below and support this point.

It is generally reported that DNA oligomers hybridized to either DNA or RNA targets adopt different helical geometries, termed B-form and A-form, respectively. These two different types of helices have dramatically different three dimensional shapes. Differences between the A- and B-helix forms may be summarized as follows: "Sin A-form duplex is generally agreed to contain sugars with a C3'-endo (N-type) pucker, in which the base pairs are inclined (tilted) approximately 19° from the helix axis and swung out from the helical axis toward the edge of the helix. As a consequence, there is greater base-base overlap in A-form structures than in B-form duplexes. In B-form duplexes of DNA, the deoxyribose sugars generally adopt a C2'-endo pucker, but with a great deal of conformational flexibility. In B-form helices, the base pairs are perpendicular to the helix axis, and are centered down the middle of the helix. There are ~ 11–12 base pairs per turn in an A-form duplex, and 10.4 base pairs for a B-form duplex." Hall, K. B., "NMR Spectroscopy of DNA/RNA Hybrids", *Current Opinion in Structural Biology* 3:336–339 (1993).

Since it is known, then, that hybrids formed with DNA and RNA targets can have dramatically different geometries, one would not expect that data obtained with DNA targets would be directly applicable to RNA targets. In fact a literature report using 2'—O-methyl RNA oligomers hybridized to DNA and RNA targets supports this point (S. M. Freier et al., "Gene Regulation of Antisense RNA and DNA", pp. 95–107, edited by R. P. Erickson and J. G. Izant, Raven Press, Ltd. New York, copyright 1992). Against DNA targets, both destabilization and stabilization were observed with the 2'—O-methyl modification to the sugar portion of the nucleosides, depending on the base sequence, because some DNA sequences favor the A-form more than others whereas stabilization was always observed against RNA targets. Moreover, we have observed dramatic differences in Tm with racemic methylphosphonate oligomers hybridized to DNA and RNA targets. This suggests that evaluations of oligomers with DNA targets may give misleading results when they are intended for use as antisense inhibitors of mRNA translation.

Thus, according to one aspect, antisense methylphosphonate (MP) Oligomers having enhanced potency as antisense inhibitors of gene expression are provided which comprise Oligomers having methylphosphonate internucleosidyl linkages enhanced for the Rp configuration. We have found that these chirally enriched MP Oligomers hybridize more tightly to RNA target sequences and also show enhanced potency in inhibiting translation of RNA targets as compared with MP Oligomers having random racemic MP internucleosidyl linkages.

In an alternate aspect, the present invention is directed to synthetic oligomers having phosphonate internucleosidyl linkages which are enriched phosphonate internucleosidyl linkages of preselected chirality and which are sufficiently complementary to a RNA target sequence to hybridize thereto. Preferred chirally enriched oligomers are those wherein greater than 40% of the phosphonate internucleosidyl linkages are chirally pure phosphonate linkages.

In a further alternate aspect, the present invention is directed to a synthetic Oligomer having enhanced potency in preventing or interfering with expression of a single stranded RNA target sequence which comprises a synthetic Oligomer enriched for Rp-configuration methylphosphonate internucleosidyl linkages which is complementary to the RNA target sequence. Preferred Rp-enriched Oligomers are those wherein greater than 40% of the methylphosphonate internucleosidyl linkages of the Oligomer are chirally pure Rp-configuration methylphosphonate internucleosidyl linkages. According to a preferred aspect, such Rp-enriched Oligomers are those which exhibit enhanced binding affinity for the RNA target sequence in comparison to an Oligomer complementary to the RNA target sequence which has random racemic methylphosphonate internucleosidyl linkages.

Accordingly, the present invention provides methods of making a synthetic Oligomer which is chirally enriched for phosphonate internucleosidyl linkages of preselected chirality (i.e. either Rp or Sp). In one aspect, this method includes the steps of identifying a single stranded target sequence and synthesizing a synthetic Oligomer enriched for phosphonate internucleosidyl linkages of preselected chirality which is sufficiently complementary to the target sequence to hybridize thereto. Suitable phosphonate internucleosidyl linkages include those selected from the group consisting of lower alkylphosphonate linkages of 1 to 3 carbon atoms and lower alkylphosphonothioate linkages of 1 to 3 carbon atoms, more preferred phosphonate linkages include methylphosphonate and methylphosphonothioate linkages. In particular, synthetic Rp-enriched MP Oligomers provided by these methods exhibit enhanced binding to an RNA target sequence. In the case of Rp-enriched MP Oligomer, provided is an Oligomer which is complementary to the identified RNA target sequence. Such Rp-enriched MP Oligomers exhibit enhanced binding to a RNA target sequence in comparison to an Oligomer complementary to the RNA target sequence having random racemic methylphosphonate internucleosidyl linkages.

According to a preferred aspect, synthetic Oligomers of the present invention may be synthesized by linking together nucleoside dimers having either a chirally pure Rp- or Sp-configuration phosphonate internucleosidyl linkage. Alternatively, trimers or tetramers having chirally pure phosphonate internucleosidyl linkages are linked together to give a chirally enriched oligomer of desired chiral enrichment, length and nucleoside base sequence.

In a further aspect, the present invention provides methods for preparing an Oligomer having a predetermined base sequence of nucleoside units and which is enriched for phosphonate linkages of preselected chirality, more preferably an oligomer which is enriched for Rp-configuration methylphosphonate and/or, as pre-selected, Rp or Sp methylphosphonothioate internucleosidyl linkages. Such method comprises linking together individual nucleoside dimer, trimer or tetramer synthons having a chirally pure phosphonate internucleosidyl linkages, said synthons having the formula:

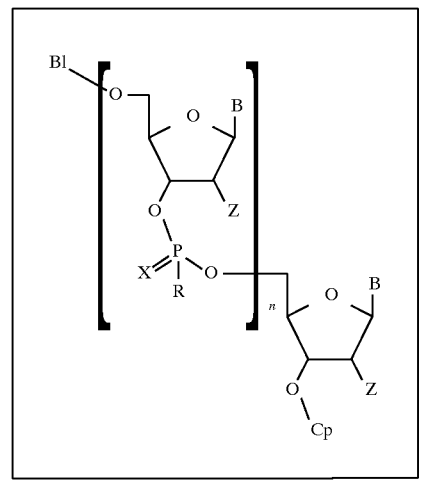

wherein X is oxygen or sulfur, R is lower alkyl of 1 to 3 carbon atoms, Z is hydrogen, alkoxy of 1 to 10 carbon atoms, halogen, or alkenyloxy of 3 to 6 carbon atoms; B is an optionally protected pyrimidine or purine base, B1 is a blocking group; Cp is a coupling group which results in a phosphonate internucleosidyl linkage when coupled to a hydroxy under coupling conditions and n is 1, 2 or 3.

Also provided are novel synthons having chirally pure phosphonate internucleosidyl linkages of the formula:

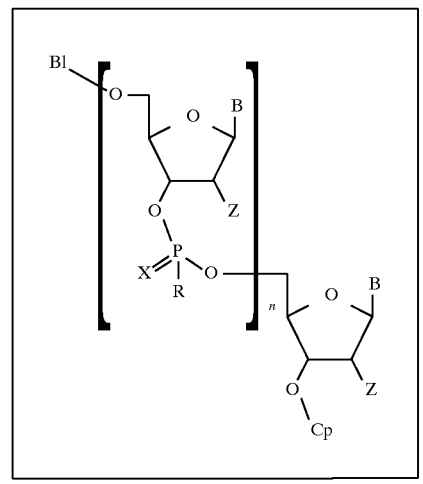

Definitions

As used herein, the following terms have the following meanings unless expressly stated to the contrary.

The term "purine" or "purine base" includes not only the naturally occurring adenine and guanine bases, but also modifications of those bases such as bases substituted at the 8-position, or guanine analogs modified at the 6-position or the analog of adenine, 2-amino purine, as well as analogs of purines having carbon replacing nitrogen at the 9-position such as the 9-deaza purine derivatives and other purine analogs.

The term "nucleoside" includes a nucleosidyl unit and is used interchangeably therewith, and refers to a subunit of a nucleic acid which comprises a 5-carbon sugar and a nitrogen-containing base. The term includes not only those nucleosidyl units having A, G, C, T and U as their bases, but also analogs and modified forms of the naturally-occurring bases, including the pyrimidine-analogs such as pseudoisocytosine and pseudouracil and other modified bases (such as 8-substituted purines). In RNA, the 5-carbon sugar is ribose; in DNA, it is a 2'-deoxyribose. The term nucleoside also includes other analogs of such subunits, including those which have modified sugars such as 2'—O-alkyl ribose.

The term "phosphonate" refers to the group

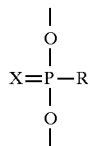

wherein X is oxygen or sulfur, R is hydrogen or an alkyl or aryl group, and thus includes various example of phosphonate and phosphonothioate internucleosidyl linkages. Suitable alkyl or aryl groups include those which do not sterically hinder the phosphonate linkage or interact with each other. The phosphonate group may exist in either an "R" or an "S" configuration. Phosphonate groups may be used as internucleosidyl linkages (or links) to connect nucleosidyl unit or a nucleosidyl unit and a non-nucleosidy monomeric unit. The term "lower alkylphosphonate" refers to groups where X is oxygen and R is lower alkyl of 1 to 3 carbon atoms. "Methylphosphonate" refers to groups where X is oxygen and R is methyl. The term "phosphonothioate" refers to those groups where X is sulfur. The term "lower alkylphosphonothioate" refers to groups where X is sulfur and R is lower alkyl of 1 to 3 carbon atoms. The term "methylphosphonothioate" refers to a phosphonothioate group wherein R is methyl.

The term "phosphodiester" or "diester" refers to the group

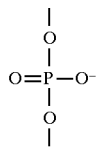

wherein phosphodiester groups may be used as internucleosidyl phosphorus group linkages (or links) to connect nucleosidyl units.

A "non-nucleoside monomeric unit" refers to a monomeric unit wherein the base, the sugar and/or the phosphorus backbone has been replaced by other chemical moieties.

A "nucleoside/non-nucleoside polymer" refers to a polymer comprised of nucleoside and non-nucleoside monomeric units.

The term "oligonucleoside" or "Oligomer" refers to a chain of nucleosides which are linked by internucleoside linkages which is generally from about 4 to about 100 nucleosides in length, but which may be greater than about 100 nucleosides in length. They are usually synthesized from nucleoside monomers, but may also be obtained by enzymatic means. Thus, the term "Oligomer" refers to a chain of oligonucleosides which have internucleosidyl linkages linking the nucleoside monomers and, thus, includes oligonucleotides, nonionic oligonucleoside alkyl- and aryl-phosphonate analogs, alkyl- and aryl-phosphonothioates, phosphorothioate or phosphorodithioate analogs of oligonucleotides, phosphoramidate analogs of oligonucleotides, neutral phosphate ester oligonucleoside analogs, such as phosphotriesters and other oligonucleoside analogs and modified oligonucleosides, and also includes nucleoside/non-nucleoside polymers. The term also includes nucleoside/non-nucleoside polymers wherein one or more of the phosphorus group linkages between monomeric units has been replaced by a non-phosphorous linkage such as a formacetal linkage, a thioformacetal linkage, a morpholino linkage, a sulfamate linkage, a silyl linkage or a carbamate linkage. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone of the non-nucleoside are either replaced by a non-nucleoside moiety or wherein a non-nucleoside moiety is inserted into the nucleoside/non-nucleoside polymer. Optionally, said non-nucleoside moiety may serve to link other small molecules which may interact with target sequences or alter uptake into target cells.

The term "alkyl- or aryl-phosphonate Oligomer" refers to Oligomers having at least one alkyl- or aryl-phosphonate internucleosidyl linkage and the remainder of the internucleosidyl linkages phosphonate internucleosidyl linkages. Suitable alkyl- or aryl-phosphonate groups include alkyl- or aryl- groups which do not sterically hinder the phosphonate linkage or interact with each other. Preferred alkyl groups include lower alkyl groups having from about 1 to about 6 carbon atoms. Suitable aryl groups have at least one ring having a conjugated pi electron system and include carbocyclic aryl and heterocyclic aryl groups, which may be optionally substituted and preferably having up to about 10 carbon atoms.

The term "methylphosphonate Oligomer" (or "MP-Oligomer") refers to Oligomers having at least one methylphosphonate internucleosidyl linkage and the remainder of the internucleosidyl linkages phosphonate linkages.

The term "neutral Oligomer" refers to Oligomers which have nonionic internucleosidyl linkages between nucleoside monomers (i.e., linkages having no positive or negative ionic charge) and include, for example, Oligomers having internucleosidyl linkages such as alkyl- or aryl- phosphonate linkages, alkyl- or aryl-phosphonothioates, neutral phosphate ester linkages such as phosphotriester linkages, especially neutral ethyltriester linkages; and non-phosphorus-containing internucleosidyl linkages, such as sulfamate, morpholino, formacetal, thioformacetal, silyl, and carbamate linkages. Optionally, a neutral Oligomer may comprise a conjugate between an oligonucleoside or nucleoside/non-nucleoside polymer and a second molecule which comprises a conjugation partner. Such conjugation partners may comprise intercalators, alkylating agents, binding substances for cell surface receptors, lipophilic agents, nucleic acid modifying groups including photo-cross-linking agents such as psoralen and groups capable of cleaving a targeted portion of a nucleic acid, and the like. Such conjugation partners may further enhance the uptake of the Oligomer, modify the interaction of the Oligomer with the target sequence, or alter the pharmacokinetic distribution of the Oligomer. The essential requirement is that the oligonucleoside or nucleoside/non-nucleoside polymer that the Oligomer conjugate comprises be substantially neutral.

The term "substantially neutral" in referring to an Oligomer refers to those Oligomers in which at least about 80 percent of the internucleosidyl linkages between the nucleoside monomers are nonionic linkages.

The term "acid resistant" refers to Oligomers which are resistant, in comparison to deoxyribooligo-nucleotides, to acid-catalyzed depurination by hydrolysis of the N-glycosyl bond.

The term "triplet" or "triad" refers a hydrogen bonded complex of the bases of three nucleosides between a base (if single stranded) or bases (if double stranded) of a target sequence, a base of a Second Strand and a Third Strand (if a single stranded target sequence) or a base of a Third Strand (if a double-stranded target).

The term "Triplex Oligomer Pair" refers to first and second Oligomers which are optionally covalently linked at one or more sites and which are complementary to and are capable of hydrogen bonding to a segment of a single stranded target nucleic acid, such as RNA or DNA, and, thus, together with the single stranded target nucleic acid, are capable of forming a triple helix structure therewith.

The term "Third Strand Oligomer" refers to Oligomers which are capable of hybridizing to a segment of a double stranded nucleic acid, such as a DNA duplex, an RNA duplex or a DNA-RNA duplex, and forming a triple helix structure therewith.

The term "complementary," when referring to a Triplex Oligomer Pair (or first and second Oligomers) or to a Third Strand Oligomer, refers to Oligomers having base sequences which are capable of forming or recognizing hydrogen bonds (and base pairing or hybridizing) with the base sequence of the nucleic acid to form a triple helix structure.

The term "substantially complementary" refers to oligomers, including Triplex Oligomer Pairs or Third Strand Oligomers which may lack a complement for each nucleoside in the target sequence, have sufficient binding affinity for the target sequence to form a stable duplex or triple helix complex, as the case may be, and thereby specifically recognize the target sequence and selectively inhibit or down-regulate its expression.

"MP(Rp)" refers to a methylphosphonate internucleosidyl linkage of Rp chirality.

"MP(PS)" refers to a methylphosphonothioate internucleosidyl linkage.

"MP(Rp)(PS)" refers to a methylphosphonothioate internucleosidyl linkage of Rp chirality.

An oligomer having "alternating MP(Rp)/MP internucleosidyl linkages" refers to an Oligomer wherein methylphosphonate linkages of Rp chirality alternate with methylphosphonate linkages of undefined chirality.

An oligomer having "alternating MP(Rp)/MP(PS) internucleosidyl linkages" refers to an oligomer wherein methylphosphonate linkages of Rp chirality alternate with methylphosphonothioate linkages of undefined chirality.

An oligomer having "alternating MP(Rp)(PS)/MP internucleosidyl linkages" refers to an oligomer wherein methylphosphonothioate linkages of Rp chirality alternate with methylphosphonate linkages of undefined (mixed) chirality.

An oligomer having "alternating MP(Rp)(PS)/MP(PS) internucleosidyl linkages" refers to an oligomer wherein methylphosphonothioate linkages of Rp chirality alternate with methylphosphonothioate linkages of undefined chirality.

A "MP(Rp)/MP dimer synthon" refers to a dinucleoside wherein the two nucleosides are linked by a mehylphosphonate internucleosidyl linkage of Rp chirality and one of the nucleosides has a 5'- or 3'-coupling group which when coupled to a 3'—OH or a 5'—OH, of another nucleoside or an oligomer will result in a methylphosphonate internucleosidyl linkage.

A "MP(Rp)/MP(PS) dimer synthon" refers to a dinucleoside wherein the two nucleosides are linked by a methylphosphonate linkage of Rp chirality and one of the nucleosides has a 5'- or 3'- coupling group which when coupled to a 3'—OH or 5'—OH of another nucleoside or an oligomer will result in a methylphosphonothioate internucleosidyl linkage.

A "MP(Rp)(PS)/MP dimer synthon" refers to a dinucleoside wherein the two nucleosides are linked by a methylphosphonothioate linkage of Rp chirality and one of the nucleosides has a 5'- or 3'- coupling group which when coupled to a 3'—OH or 5'—OH of another nucleoside or an oligomer will result in a methylphosphonate internucleosidyl linkage.

A "MP(Rp)(PS)/MP dimer synthon" refers to a dinucleoside wherein the two nucleosides are linked by a methylphosphonothioate linkage of Rp chirality and one of the nucleosides has a 5'- or 3'- coupling group which when coupled to a 3'—OH or 5'—OH of another nucleoside or an oligomer will result in a methylphosphonothioate internucleosidyl linkage.

A "2'—O-methyl MP(Rp)/2'—O-methyl MP dimer synthon" refers to a dinucleoside wherein two 2'—O-methyl nucleosides are linked by a methylphosphonate linkage of Rp chirality and one of the nucleosides has a 5'- or 3'-coupling group which when coupled to a 3'—OH or 5'—OH of another nucleoside or an oligomer will result in a methylphosphonate internucleosidyl linkage.

DETAILED DESCRIPTION OF THE INVENTION

Figure 1:
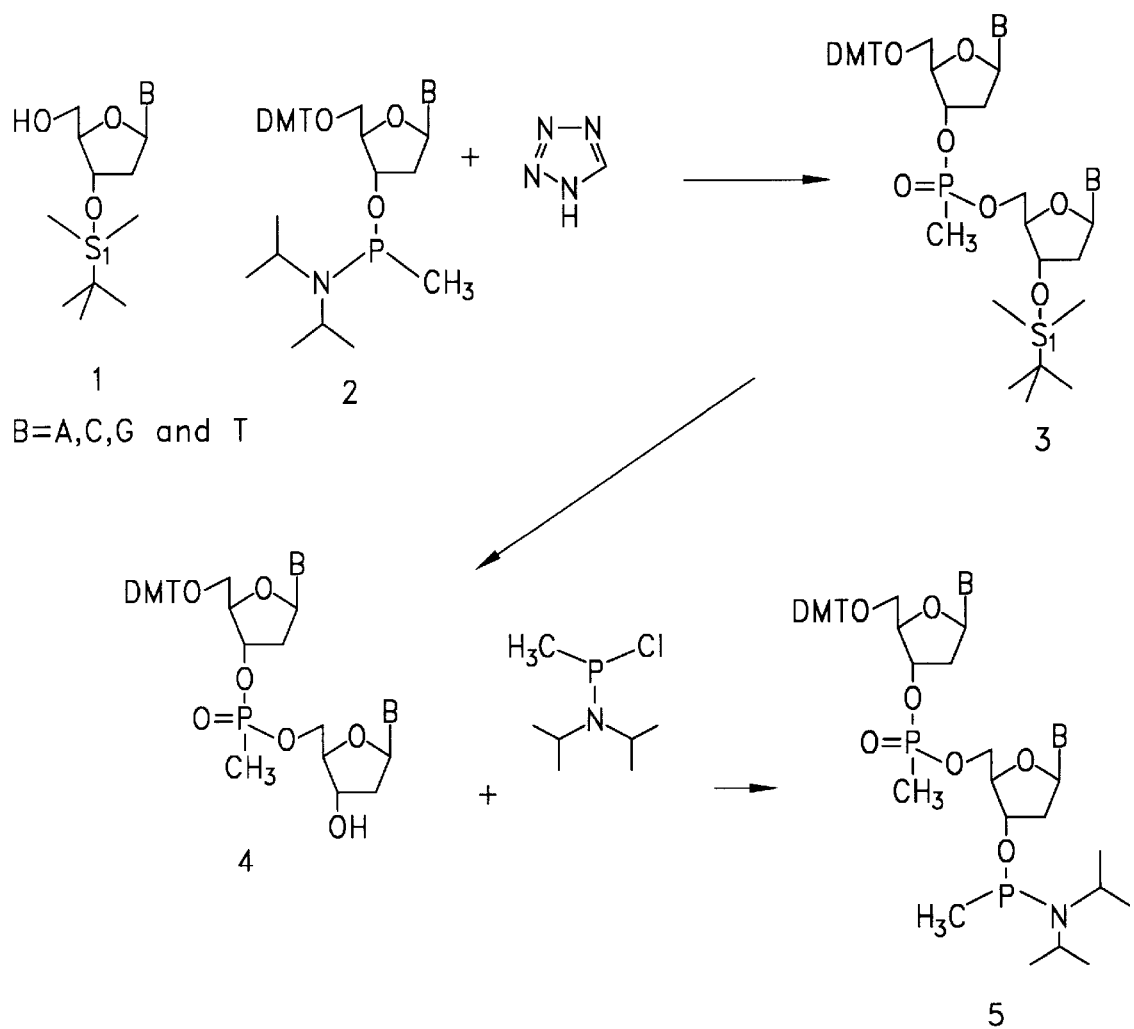
FIG. 1 depicts a synthetic scheme for the preparation of nucleoside dimers.

The phosphonate internucleosidyl linkages in synthetic Oligomers of the present invention contain a lower alkyl group replacing one of the two non-bonding (or non-bridging) oxygens on the phosphorus of a phosphodiester internucleosidyl linkage, the other non-bonding oxygen remains or is alternatively replaced by sulfur. The replacement of oxygen by lower alkyl creates a chiral environment at the phosphorus which can be designated as either Rp or Sp, depending on which of the non-bridging (or non-bonding) oxygens has been replaced with lower alkyl. The Rp and Sp configurations can be depicted as follows:

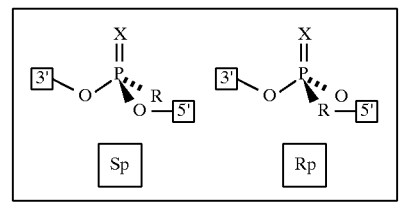

Since these Oligomers are capable of having either Rp or Sp chirality at each phosphorus, a particular Oligomer theoretically can have $2^n$ different diastereomeric forms where n is the number of phosphonate internucleosidyl linkages in the Oligomer. For example, an Oligomer having a total of 10 phosphonate internucleosidyl linkages theoretically has 1,024 diastereomers and an Oligomer having a total of 18 phosphonate internucleosidyl linkages theoretically has 262,144 diastereomers.

By providing Oligomers enriched for a particular configuration of phosphonate internucleosidyl linkages, the number of diastereomers for a particular Oligomer is decreased. Thus, in one aspect, the present invention is directed to methods of synthesizing oligomers enriched for phosphonate internucleosidyl linkages of preselected chirality, according to a preferred aspect, oligomers enriched for Rp configuration lower alkylphosphonate internucleosidyl linkages, more preferably, enriched for Rp-configuration MP internucleosidyl linkages, and, in particular, Oligomers having a number of chirally pure phosphonate internucleosidyl linkages.

According to one synthetic method, nucleoside dimers having a phosphonate internucleosidyl linkage connecting the two nucleosidyl units of the dimer are prepared and separated into their Rp and Sp isomers. The resulting dimers which have a defined chirality at the phosphonate are then derivatized to give dimer synthons so that they may be coupled together using an automated DNA synthesizer (see, e.g., Examples 1 to 4). The dimer synthons have coupling groups which allow them to be coupled together to give a chirally enriched phosphonate oligomer (see Examples 5 to 13). From a stock of 16 dimers, Oligomers of any nucleoside base sequence may be synthesized by linking together the appropriate dimers. Dimers are added to the growing Oligomer chain until an Oligomer having the desired number of nucleosides is obtained. The resulting Oligomer has a defined chirality at every other internucleosidyl linkage (i.e., those linkages originally derived from the internucleosidyl linkages of the coupled dimeric units). The remaining phosphonate internucleosidyl linkages may comprise a mixture of Rp and Sp configurations.

Alternatively, larger blocks of nucleosides such as trimers and tetramers may be coupled to give a chirally enriched oligomer. Trimers having two chirally pure internucleosidyl linkages may be conveniently prepared by coupling the appropriate chirally pure dimer synthon to another nucleoside and, for example, if Rp chirality is selected for, then separating the resulting Rp-Rp and Rp-Sp trimers. The resulting trimer has defined chirality (i.e., is chirally pure) at both internucleosidyl linkages. The trimers are then derivatized to give trimer synthons so that they may be coupled together using an automated DNA synthesizer. The trimer synthons have coupling groups which allow them to be coupled together to give a chirally enriched phosphonate oligomer. (See Examples 14 and 15). From a stock of 64 trimers, oligomers of any base sequence may be synthesized by linking together the appropriate trimers. Trimers may be sequentially added to the growing oligomer chain or alternatively coupled with nucleoside monomers, dimers and/or tetramers until an oligomer having the desired number of nucleosides is obtained. The resulting oligomer has a defined chirality at those internucleosidyl linkages derived from the internucleosidyl linkages of the coupled dimers, trimers or tetramers, the remaining phosphonate internucleosidyl linkages may comprise a mixture of Rp and Sp configurations. Thus, use of these trimers will result in an oligomer having linkages of defined chirality at about two out of every three internucleosidyl linkages. By following analogous techniques, tetramers having three chirally pure internucleosidyl linkages may be prepared and coupled to each other to give oligomers. Alternatively, dimers, trimers and other short oligomers having internucleosidyl linkages of defined chirality (such as pure Rp) may be coupled together in appropriate sequence to give an oligomer of a particular desired sequence and length.

According to an alternate synthetic method, coupling conditions for nucleoside synthons (or dimer synthons) are used which direct coupling to give an enhanced yield of the desired chiral configuration, for example Rp with methylphosphonate internucleosidyl linkages. Such a method may be used to couple individual nucleoside synthons or alternatively the chirally pure dimers and, thus, obtained are Oligomers enriched for the desired chirality at each phosphonate internucleosidyl linkage, for example the Rp configuration with methylphosphonate internucleosidyl linkages.

Preferred Dimer and Trimer Synthons

The chirally pure methylphosphonate dimer and trimers can be coupled to form methylphosphonate and methylphosphonothioate oligomers by several methods. The 3' OH of chirally pure methylphosphonate dimer and trimers of Examples 1, 2, and 14 can be converted to the phosphotriester synthon (using reported methods), a phosphoramidite synthon (as described in the examples), an H-phosphonate synthon (see, Seela, F. and Kretschmer, U. (1991) J. Org. Chem. 56:3861–3869), or a phosphoromonochloridite reagent (see, Loschner, T. and Engels, J. (1989) Tet. Lett. 30, 5587–5590).

These dimer synthons include:

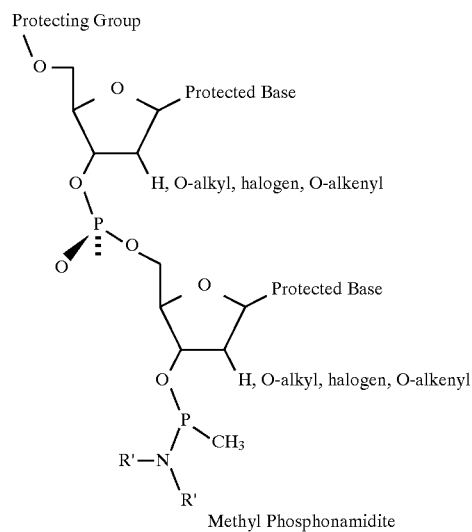

Methyl Phosphonamidite

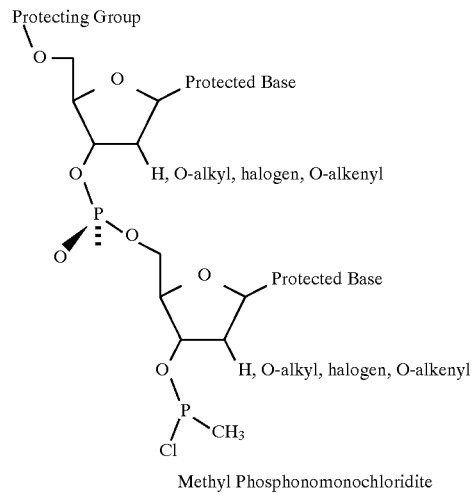

Methyl Phosphonomonochloridite

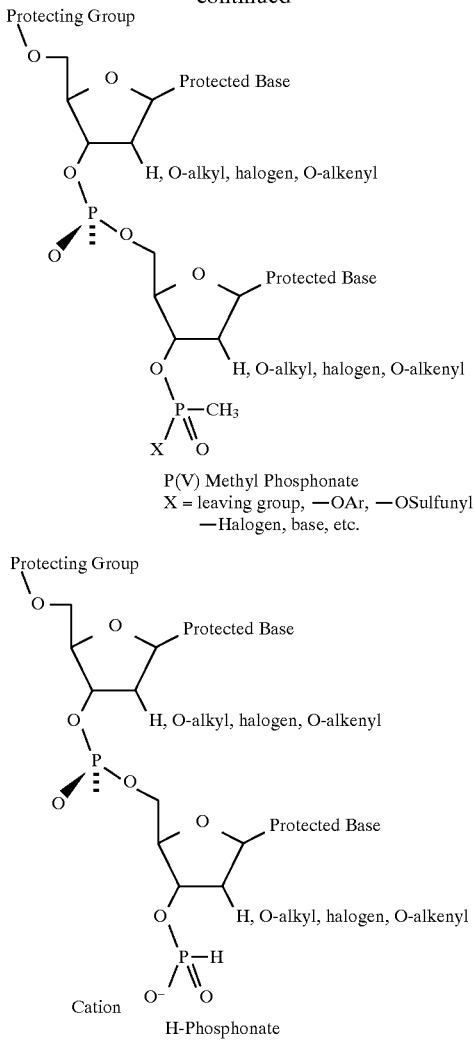

Utility and Administration

The Oligomers provided herein may form a high affinity complex with a target sequence such as a nucleic acid with a high degree of selectivity. In addition, derivatized Oligomers may be used to bind with and then irreversibly modify a target site in a nucleic acid by cross-linking (psoralens) or cleaving (EDTA). By careful selection of a target site for cleavage, one of the strands may be used as a molecular scissors to specifically cleave a selected nucleic acid sequence.

The Oligomers provided herein may be derivatized to incorporate a nucleic acid reacting or modifying group which can be caused to react with a nucleic acid segment or a target sequence thereof to irreversibly modify, degrade or destroy the nucleic acid and thus irreversibly inhibit its functions.

These Oligomers may be used to inactivate or inhibit or alter expression of a particular gene or target sequence of the same in a living cell, allowing selective inactivation or inhibition or alteration of expression. The target sequence may be RNA, such as a pre-mRNA or an mRNA. mRNA target sequences include an initiation codon region, a coding region, a polyadenylation region, an mRNA cap site or a splice junction.

Since the Oligomers provided herein may form duplexes or triple helix complexes or other forms of stable association with transcribed regions of nucleic acids, these complexes are useful in "antisense" or triple strand therapy. "Antisense" therapy as used herein is a generic term which includes the use of specific binding oligomers to inactivate undesirable DNA or RNA sequences in vitro or in vivo.

Many diseases and other conditions are characterized by the presence of undesired DNA or RNA, which may be in certain instances single stranded and in other instances double stranded. These diseases and conditions can be treated using the principles of antisense therapy as is generally understood in the art. Antisense therapy includes targeting a specific DNA or RNA target sequence through complementarity or through any other specific binding means, in the case of the present invention by formation of duplexes or triple helix complexes.

According to one aspect of the present invention, these antisense Oligomers have a sequence which is complementary to a portion of the RNA transcribed from the selected target gene. Although the exact molecular mechanism of inhibition has not been conclusively determined, it has been suggested to result from formation of duplexes between the antisense Oligomer and the RNA transcribed from the target gene. The duplexes so formed may inhibit translation, processing or transport of an mRNA sequence.

According to an alternate aspect of the present invention, interference with or prevention of expression or translation of a selected RNA target sequence may be accomplished by triple helix formation using Oligomers of the present invention as a Triplex Oligomer Pair having sequences selected such that the Oligomers are complementary to and form a triple helix complex with the RNA target sequence and thereby interfere with or prevent expression of the targeted nucleic acid sequence. Such triple strand formation can occur in one of several ways. Basically, two separate or connected Oligomers may form a triple strand with the single stranded RNA. Further descriptions of the use of Oligomers (including Triplex Oligomer Pairs) to prevent or interfere with the expression of a target sequence of double or single stranded nucleic acid by formation of triple helix complexes is described in the U.S. patent applications Ser. No. 07/388,027, now U.S. Pat. No. 4,972,667; Ser. No. 07/751,813, now U.S. Pat. No. 5,665,541; Ser. Nos. 08/485, 641 and 07/987,746 now abandoned, the disclosures of which are incorporated herein by reference.

As a general matter, the Oligomers employed will have a sequence that is complementary to the sequence of the target nucleic acid. However, absolute complementarity may not be required; in general, any Oligomer having sufficient complementarity to form a stable duplex (or triple helix complex as the case may be) with the target nucleic acid is considered to be suitable. Since stable duplex formation depends on the sequence and length of the hybridizing oligomer and the degree of complementarity between the antisense Oligomer and the target sequence, the system can tolerate less fidelity (complementarity) when longer Oligomers are used. This is also true with Oligomers which form triple helix complexes. However, Oligomers of about 8 to about 40 nucleosidyl units in length which have sufficient complementarity to form a duplex or triple helix structure having a melting temperature of greater than about 40° C. under physiological conditions are particularly suitable for use according to the methods of the present invention.

With respect to single stranded target sequences, we have found that two strands of a methylphosphonate Oligomer of the present invention (Second and Third Strands) and one strand of a complementary synthetic RNA Oligomer (First Strand) form a triple helix complex. According to our experiments, the two methylphosphonate strands bind in a parallel orientation. Experiments demonstrated triple helix formation with methylphosphonate Oligomers of a sequence of A and G nucleosides. (See Example 23).

These triple helix complexes formed by binding a target single stranded RNA and two methylphosphonate Oligomers show high affinity. Formation of these triple helix complexes has been shown to dramatically inhibit translation at sub-micromolar concentrations.

The triple helix complexes can be formed using Oligomers containing naturally occurring bases (i.e., A, C, G, T or U). Alternatively, if desired for increased stability, certain stabilizing bases such as 2-amino A (for A) or 5-methyl C may be used in place of the corresponding naturally occurring base. These bases may increase stability of the triple helix complex by having increased hydrogen bonding interactions and stacking interactions with other bases. Increased stability may result in increased affinity constants which increase potency.

The Oligomers for use in the instant invention may be administered singly, or combinations of Oligomers may be administered for adjacent or distant targets or for combined effects of antisense mechanisms with the foregoing general mechanisms.

In therapeutic applications, the Oligomers can be formulated for a variety of modes of administration, including oral, topical or localized administration. It may be beneficial to have pharmaceutical formulations containing acid resistant Oligomers that may come in contact with acid conditions during their manufacture or when such formulations may themselves be made acidic, to some extent, in order to more compatible with the conditions prevailing at the site of application, e.g., the acid mantle of the skin. Techniques and formulations generally may be found in *Remington's Pharmaceutical Sciences*, Mack Publishing Co., Easton, Pa., latest edition. The Oligomer active ingredient is generally combined with a carrier such as a diluent or excipient which may include fillers, extenders, binding, wetting agents, disintegrants, surface-active agents, erodible polymers or lubricants, depending on the nature of the mode of administration and dosage forms. Typical dosage forms include tablets, powders, liquid preparations including suspensions, emulsions and solutions, granules, and capsules.

Certain of the Oligomers of the present invention may be particularly suited for oral administration which may require exposure of the drug to acidic conditions in the stomach for up to about 4 hours under conventional drug delivery conditions and for up to about 12 hours when delivered in a sustained release from. For treatment of certain conditions it may be advantageous to formulate these Oligomers in a sustained release form. U.S. Pat. No. 4,8:39,177 to Colombo et al., the disclosure of which is incorporated herein by reference, describes certain preferred controlled-rate release systems. For oral administration, these Oligomers may preferably have 2'—O-alkyl, more preferably 2'—O methyl, nucleosidyl units; these Oligomers are formulated into conventional as well as delayed release oral administration forms such as capsules, tablets, and liquids.

The oligomers having 2'—O-alkyl nucleosidyl units advantageously exhibit enhanced stability at low (acid) pH and, thus, may be particularly suited for formulation in preparations for topical administration. Since the skin has an acid mantle, formulations including these acid resistant Oligomers may prove advantageous. This also can be advantageous in light of the finding that neutral Oligomers will cross skin and mucous membranes as described in U.S. patent application Ser. No. 07/707,879, now abandoned, which is incorporated by reference. Also it may be desirable to provide formulations which include acidic media when using acid-resistant neutral Oligomers.

For topical administration, the Oligomers for use in the invention are formulated into ointments, salves, eye drops, gels, or creams, as is generally known in the art.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucusal administration. In addition, detergents may be used to facilitate permeation. Transmucosal administration may be through use of nasal sprays, for example, as well as formulations suitable for administration by inhalation, or suppositories.

To assist in understanding the present invention, the following examples are included which describe the results of a series of experiments. The following examples relating to this invention should not, of course, be construed in specifically limiting the invention and such variations of the invention, now known or later developed, which would within the purview of one skilled in the art are considered to fall within the scope of the present invention as hereinafter claimed.

EXAMPLES

Example 1

Preparation of a MP(Rp)/MP Dimer Synthon

A. Preparation of a (CT) Dimer Having a Chirally Pure Methylphosphonate Internucleosidyl Linkage Using Solution Phase Chemistry Into a 2 L roto-evaporator flask was placed 10.0 g (28 mM) of 3'-tert-butyldimethylsilyl thymidine and 26.1 g (35 mM) of 5'-dimethoxytrityl-$N^4$-isobutyryl-3'-methyl-N,N-diisopropylaminophosphoramidite-2'-deoxycytidine. The solids were dissolved in 500 ml of acetonitrile and evaporated to dryness under vacuum. This process was repeated with another 500 ml of acetonitrile and then the flask was released under argon and stoppered with a rubber septa.

This dry solid foam was then dissolved in 500 ml of acetonitrile ("ACN"), and with manual stirring, treated all at once with 404 ml tetrazole (180 mM, 0.45M tetrazole in THF). Manual stirring is continued for 30 seconds and then the flask is allowed to stand for another 2.5 minutes, after which time the reaction mix is treated all at once with 275 ml of an oxidizer solution ($I_2/H_2O$/lutidine/THF; 25 g/2.5 ml/100 ml/900 ml). The solution was stirred manually and allowed to stand at room temperature for 15 minutes. The resulting dark amber solution was then treated with bisulfite (2 g/25 ml/$H_2O$), which upon addition, turned the solution light amber as it reacted with the excess iodide. The reaction mix was then concentrated to a thick oil and taken up in ethyl acetate ("EtOAc") (500 ml) and washed with saturated sodium bicarbonate (2×250 ml) and $H_2O$ (2×250 ml). The organic phase was dried over $MgSO_4$, filtered and concentrated to a light colored solid foam, which upon further drying yielded 35 grams of crude dimer.

The crude dimer was run on HPLC (reverse phase, Waters C18 bondapak) with a program (ACNMETH) starting with 50% acetonitrile and 0.1M triethylammonium acetate (TEAA, pH~7.0) which increased to 100% acetonitrile over 20 minutes with a linear gradient. Two major peaks were resolved, one at 4.5 minutes, which is residual lutidine and the other at 14.5 minutes which is the mixture of Rp and Sp diastereomers. The ratio of Rp and Sp was determined quantitatively by taking a 5 mg aliquot of the crude product and dissolving it in 1.5 ml of acetonitrile along with 0.5 ml of tetrabutylammonium fluoride (TBAF, 1M solution in THF). After standing at room temperature for 10 minutes the sample was run on HPLC. Two new peaks were observed at 6.5 and 7.1 minutes and the later eluting peak was gone. The first new peak, which is believed to be the Sp diastereomer, represented 66% (2/1) of the normalized value for the two peaks. The crude product was also analyzed by the (normal phase silica plate) in 75/25 EtOAc/$CH_2Cl_2$ ("75/25") with 5% methanol added. The tlc showed two spots with Rf's of 0.45 and 0.64, respectively; the faster running product (believed to be the Rp form) was less intense than the slower moving one.

The Rp diastereomer wits separated on normal phase silica using a methanol step gradient in 75/25 EtOAc/$CH_2Cl_2$. A 7.5 cm by 65 cm column, was loaded with 700 g of silica (first slurried in 2.5 L of neat 75/25 EtOAc/$CH_2Cl_2$). The crude dimer was then dissolved in 75 ml of 75/25 EtOAc/$CH_2Cl_2$ and loaded onto the column. The column was started with 1% methanol and increased to 2% and finally 3% where the Rp dimer began to elute. The Rp dimer eluted cleanly over several bed volumes while maintaining 3% methanol in the eluent. The Sp dimer was eluted later with 30% methanol. The Rp dimer yield was 11.0 grams, while the Sp yield was 17.8 grams. HPLC analysis (ACNMETH) was performed on the Rp dimer and one peak was observed at 14.5 minutes. The tlc (75/25 EtOAc/$CH_2Cl_2$, 5% methanol) of this product, revealed a single spot product with an Rf of 0.55 which, upon treatment with 10% sulfuric acid in ethanol and heat, was both trityl and sugar positive.

The newly resolved Rp dimer, 11.0 g (0.011M) was dissolved in 110 ml of ACN and treated all at once at room temperature with 22 ml of TBAF (0.022M, 1M in THF). The reaction mix was allowed to stand overnight at ambient temperature. The next morning the reaction was determined to be complete by tlc (75/25 EtOAc/$CH_2Cl2$ with 10% methanol); no starting material was detected but a small amount of 5'-DMT-dT was observed, which runs considerably faster on normal phase silica than the 3'—OH of the dimer. The reaction mixture was concentrated on a rotary evaporator to a thick oil which was then dissolved in $CH_2Cl_2$ (200 ml) and washed with saturated sodium bicarbonate (2×100 ml) and $H_2O$ (2×100 ml). The organic phase was dried over $MgSO_4$, filtered, and concentrated to a light yellow solid foam, which was purified on 100 grams of silica (75/25, EtOAc/$CH_2Cl_2$ with 5% methanol). The 5'-DMT-dT was removed but an impurity at 13.5 minutes (HPLC, ACNMETH) was detected which was first believed to be unreacted starting material (t-BDMS on) but after additional treatment with TBAF this was found not to be the case. A second column, using 100 g of silica and the same eluent was run and smaller fractions were taken; the column was able to successfully separate the two spots. The pure CT-Rp dimer fractions were pooled and concentrated to yield 5.5 grams of a nearly white solid foam.

B. Preparation of a Chirally Pure Dimer Synthon

The CT-3'—OH dimer, 5.5 g (6 mM), prepared as described and hereinabove, was rendered anhydrous with two co-evaporations with pyridine. The resulting solid foam was released from the rotary evaporator with argon and stoppered with a rubber septa. The solid foam was dissolved in 100 ml of 9/1, ACN/$CH_2Cl_2$, then treated with 1.7 ml triethylamine (TEA, 12 mM). With magnetic stirring, the reaction mix was treated dropwise at room temperature with 1.5 ml chloromethyl-N,N-diisopropylamino phosphine (Cl-MAP, 8 mM). The reaction was monitored on HPLC (ACNMETH) and after 1.5 hours was complete, showing two main products, one at 3.5 minutes which was pyridine and a second at 14.3 minutes which was the desired amidite.

The reaction mixture was concentrated on a rotary evaporator using a partial vacuum; the flask which contained the resulting light amber sludge was released under argon and capped. The crude product was immediately passed through a flash column containing 60 grams of silica (first equilibrated in 1/1/1 ACN/EtOAc/$CH_2Cl_2$ with 3% TEA). The product was eluted quickly with this eluent and all U.V. positive fractions were pooled and concentrated. The resulting solid foam was co-evaporated with ACN to remove any residual TEA, then dried overnight under full vacuum. The final product, an off white solid foam, weight 5.0 grams.

Example 2

Preparation of 2'—O-Methyl MP(Rp)/2'—O Methyl MP Dimer Synthons

A. Preparation of 2'—O-Methyl-C-Monomer

A 5.0 g (8 mmol) portion of 2'—O methyl cytidine was rendered anhydrous with pyridine co-evaporations (3×25 ml) and then dissolved in 50 ml acetonitrile. The solution was treated with 1.65 ml triethylamine ("TEA") (12 mmol, 1.5 eq.) and cooled in an ice bath. The solution was then treated with dropwise addition of 1.65 ml chloromethyl-N, N-diisopropylamino phosphine ("Cl-MAP") over two minutes. The ice bath was removed and the reaction mixture stirred for two hours. The reaction mixture (reaction was determined to be complete by HPLC) was concentrated to dryness. The residue was dissolved in 20 ml ethyl acetate/heptane (1:1) with 4% TEA, then loaded onto 40 g silica gel equilibrated with the same solvent system. All UV absorbing (λ?) eluent from the column was collected and pooled, then concentrated to give 5.5 g of the above-identified product (yield about 90%).

B. Preparation of Silyl-Protected 2'—O-Methyl Uridine

Into a 250 ml round bottom flask was placed 5.0 g (9.0 mmol) 5'-DMT, 2'O-methyl uridine which was rendered anhydrous with dimethylformamide (DMF) co-evaporations (3×25 ml). The resulting dry foam was taken up in 50 ml DMF, then treated all at once with 2.4 g (35 mmol, 3.9 eq.) imidazole, followed by dropwise addition of 3.0 ml (12 mmol, 1.3 eq.) t-butyldiphenylsilyl chloride. The reaction mixture was stirred at room temperature overnight.

The progress of the reaction was checked by HPLC (ACN method: Solution A was 50/50 ACN/0.1M TEAA in water, pH 7 and Solution B was ACN. A gradient of 0 to 100% Solution B was run at a rate of 1 ml/minute over 25 minutes) and thin layer chromotography ("TLC") using 5% methanol in methylene chloride, and determined to be complete (no starting material was evident). The reaction mixture was then poured into ice water and taken up in methylene chloride, then washed several times with aqueous sodium bicarbonate and water. The organic phase was dried over magnesium sulfate, filtered and then concentrated to give 7.2 g of a solid foam which gave a single spot on TLC. The solid foam was then dissolved in 70 ml metthylene chloride and treated (with rapid magnetic stirring) all at once with 70 ml. benzene sulfonic acid, 2% by weight in 2:1 methylene chloride/methanol. After stirring for 15 minutes at room temperature, the reaction mixture was quenched with 10 ml TEA. The resulting detrilylated compound was stripped down to a thick amber oil which was then loaded onto 150 g. silica gel equilibrated in heat methylene chloride. The product was eluted from the column using 2% methanol in methylene chloride. After drying, 3.51 g of the above identified product were obtained (yield about 80%).

C. Preparation of 2'—O-Methyl CU MP(Rp)/MP Dimer

The silyl-protected 2'—O methyl uridine monomer (product of Example 2B) (3.0 g, 6 mmol) was taken up in 30 ml anhydrous ACN. The 2'—O methyl cytidine amidite monomer (product of Example 2A) (5.5 g, 7 mmol, 1.2 eq.) separately, was taken up in 55 ml ACN. Both solutions were allowed to stand over 3 Å molecular sieves overnight at room temperature.

The two solutions were carefully decanted into a single flask and treated with 94 ml tetrazole (0.45M in ACN, 42 mmol, 7 eq). The resulting mixture was stirred for 4 minutes and then oxidized by addition of 1.5 ml (1.2 eq.) cumene hydroperoxide. The reaction mixture was concentrated to dryness, then taken up in methylene chloride and washed with aqueous sodium bicarbonate and water. The organic phase was dried over magnesium sulfate, filtered and concentrated to give 7.5 g. of a solid foam. The diastereomeric ratio as determined by HPLC by comparison of areas under the peaks, was 57/43 Sp to Rp.

The Rp diastereomer was isolated by column chromatography using two silica columns (100:1, silica to crude product, equilibrated in 3:1 ethylacetate/methyl chloride with an increasing methanol gradient from 1 to 5%). A total of 1.07 g of pure Rp dimer was isolated.

D. Deprotection of 2'—O-Methyl CU MD(Rp)/MP Dimer

A 1.07 g (0.90 mmol) portion of the 2'—O methyl CU dimer (product of Example 2C) was dissolved in 10 ml THF and treated all at once with 1.5 ml (1 m in THF, 1.5 eq.) tetrabutylammonium fluoride ("TBAF"). The reaction mixture was stirred at room temperature of r 30 minutes after which time HPLC revealed complete deprotection of the silyl group had been achieved. The reaction mixture was concentrated and the concentrate purified on 10 g silica gel, eluting with 3:1 ethyl acetate/methylene chloride with 5% methanol. The clean fractions were concentrated to give 550 mg of the above-identified pure 5'—OH dimer.

E. Preparation of Chirally Pure 2'—O-Methyl CU MP(Rp)/MP) Dimer Synthon

Into a 100 ml round bottom flask was placed 400 mg (0.372 mmole) of 2'—O methyl CU dimer (product of Example 2D); it was rendered anhydrous by 1×5 ml co-evaporation with acetonitrile. The dry foam was then released from the vacuum system under argon gas, dissolved in 4 ml ACN and stoppered with a rubber septa. The solution was treated with 2 equivalents TEA (103 µl, 0.744 mmol), followed by 1.75 equivalents chloro-methyl-N,N-diisopropyl phosphine ("Cl-MAP") (118 µl, 0.651 mmol). The reaction mixture was stirred for 1 hour at room temperature, after which time HPLC showed about 50/50 starting material/product. An additional 50 µl TEA and 70 µl Cl-MAP were then added and the mixture stirred for an hour. When HPLC showed only 80% conversion, an additional 30 µl TEA and 30 µl Cl-MAP were added and the resulting mixture stirred another hour. At this time HPLC revealed 6% starting material. The reaction mixture was concentrated to dryness. The residue was dissolved in 500 ml 3/1/3 ethylacetate/acetonitrile/methylene chloride with 4% TEA and loaded onto 5 g silica equilibrated in the same solvent system. Fractions were collected. The early fractions were contaminated with a yellow impurity and, thus, were pooled and concentrated separately. The product from those fractions was then repurified by chromatography using the same conditions and pooled with the clean product isolated from the first column. The combined products were co-evaporated with ACN (3×5 ml) and dried overnight under full vacuum to give 350 mg (77% yield) of the above identified product which HPLC showed to be 95.5% pure.

Example 3

Preparation of 2'—O-Methyl-MP(Rp)(PS)/2'—O-Methyl-MP Dimer Synthons

These dimer synthons are prepared by following the procedures described in Example 2, except that in Paragraph C, an equivalent amount of 3H-1,2-benzodithiole-3-one,1,1-dioxide (Beaucage reagent) is substituted for cumene hydroperoxide.

Example 4

Preparation of MP(Rp)(PS)/MP Dimer Synthons

These dimer synthons are prepared by following the procedures of Example 1, except in Paragraph A, an equivalent amount of 3-H-1,2-benzodithiole-3-one, 1,1-dioxide (Beaucage reagent) is substituted for the oxidizer solution ($I_2/H_2O$/lutidine/THF)

Example 5

Preparation of 5'-(T*A)-(G*C )-(T*T)-(C*C)-(T*T)-(A*G)-(C*T)-(C*C)-(TG)-C-3'

The grouped dinucleosides indicate coupled dimers and the asterisk indicates where the stereochemistry is fixed (chirally defined or chirally pure) as the fast eluting isomer on silica gel (identified as Rp).

An Oligomer having this sequence was synthesized using the appropriate protected dinucleotide methylphosphonamidites prepared using methods such as those described in Example 1 above. Manual couplings were used to synthesize the oligomer to conserve reagent, although the process can be done on an automated DNA synthesizer using the protocol described in Example 7 from the 3' terminus starting with support-bound cytidine.

Each of the desired protected dinucleotide methylphosphonamidites (22 mg each per required coupling), T*A, G*C, T*T (2x), C*C (2x), A*G, C*T, and T*G, freshly co-evaporated with pyridine and toluene to ensure dryness, was placed into a dried 1 ml glass autosampler vial and dissolved with anhydrous acetonitrile to give a concentration of 0.1M (200 µl were used per coupling). The vials were purged with argon and tightly sealed with screw caps with teflon septa.

A 1 µmole scale Milligen DNA synthesis column was filled with 1 µmole of support bound cytidine. The column was attached to a ring stand in a vertical orientation. A male-male leur fitting was attached to the bottom along with an 18 gauge needle to control the effluent. The column was washed with 10 ml of ACN using a syringe. The support bound nucleoside was then detrilylated by passing 3 ml of 2% dichloroacetic acid in dichloromethane through the column over 1.5 minutes. The orange, dimethoxytrityl cation bearing solution was reserved. The column was washed twice with 10 ml each of ACN (anhydrous).

The first coupling was accomplished by passing 10 ml more ACN (anhydrous) through the column. Then, 200 µl of the TG methylphosphonamidite was drawn into a 1 ml syringe. Next, 200 μL of 0.45M tetrazole in anhydrous ACN was likewise drawn into the syringe containing the methylphosphonamidite. The reagents were rapidly mixed in the syringe, then slowly passed through the column dropwise over 3 minutes, being sure to lightly draw the plunger up and down to ensure adequate mixing with the support. After 3 minutes, 1 ml of the oxidizing reagent (0.1M $I_2$ in 74.25% THF, 25% 2,6-lutidine, and 0.25% water) as passed through the column over 1 minute. The column was then washed with 20 ml of ACN. The column was then treated for 1 minute with 600 μl of a solution containing 20% (v/v) acetic anhydride, 30% (v/v) ACN, 50% (v/v) pyridine, and 0.312% (w/v) dimethyaminopyridine. The column was washed with 20 ml of ACN.

The synthetic cycle was then repeated with each dinucleotide methylphosphonamidite until the synthesis was completed. The order of addition of dimers after the initial T*G coupling was C*C, C*T, A*G, T*T, C*C, T*T, G*C, and T*A.

The dimethoxytryl group was removed from the oligomer at the end of the synthesis.

The oligomer was then cleaved from the support and deprotected. The support bound oligomer was removed from the synthesis cartridge and placed in a glass 1 dram vial with a screw top. The support was treated for 30 minutes at room temperature with 1 ml of a solution of acetonitrile/ethanol/ $NH_4OH$ (9/9/1). Then, 1 ml of ethylenediamine was added to the reaction vessel and the reaction mixture allowed to sit for 6 hours at ambient temperature in order to go to completion. The supernatant containing the oligomer was then removed from the support and the support was rinsed twice with 1 ml of 1/1 acetonitrile/water; the washings were combined with the supernatant. The combined solution was diluted to 50 ml total volume with water and neutralized with approximately 1.7 ml of glacial acetic acid. The neutralized solution was desalted using a Waters C-18 Sep-Pak cartridge which was pre-equilibrated with 5 ml acetonitrile, 5 ml of 50% acetonitrile/water, and 5 ml of water, sequentially. After the reaction solution was passed through the column, it was washed with 50 ml of water. The product was then eluted with 2 ml of 1/1 acetonitrile/water.

The oligomer was purified by HPLC on a reverse phase column (Poros II R/H 4.6×100 mm) using a gradient of acetonitrile in water.

Coupling efficiencies are set forth in Table I below.

TABLE I

Coupling Efficiencies of
Dinucleotide Methylphosphonamidites

| Dinucleotide | Coupling Efficiency |
|---|---|
| T*G | 99.7% |
| C*C | 90.2% |
| C*T | 91.8% |
| A*G | 85.5% |
| T*T | 97.8% |
| C*C | 83.6% |
| T*T | 100% |
| G*C | 86.2% |
| T*A | 92.4% |

Example 6

Preparation of 5'-(G*T)-(C*T)-(T*C)-(C*A)-(T*G)-(C*A)-(T*G)-(T*T)-(G*T)-C-3'

The grouped dinucleotides indicate coupled dimers and the asterisk indicates where the stereochemistry is fixed.

This sequence was synthesized using the appropriate protected Rp dinucleotide methylphosphonamidites prepared and isolated using procedures such as those described in Example 1 above. Manual couplings were used to synthesize the oligomer in order to conserve reagent. However, if desired, the process can be done on an automated DNA synthesizer using the protocol described in Example 7. The sequence was synthesized from the 3' terminus starting with methaacrylate support bound 2'-deoxycytidine.

Each of the desired protected dinucleotide methylphosphonamidites (100 mg), G*T, T*T, T*G, C*A, T*G, C*A, T*C, C*T, and G*T was placed into a dried 3 ml glass conical vial and dissolved with anhydrous acetonitrile to a concentration of 0.1M. Molecular sieves (3 Å) (0.5 ml volume) were added to each vessel, the vessels purged with argon, and tightly sealed with screw caps with teflon septa. The reagents were allowed to stand overnight prior to use.

A 1 μmole scale Milligen DNA synthesis column was filled with 1 μmole of methacrylate support bound 2'-deoxycytidine. The column was attached to a ring stand in a vertical orientation. A male—male luer fitting was attached to the bottom along with an 18 gauge needle to control the effluent. The column was washed with 10 ml of ACN using a syringe. The support bound nucleoside was then detritylated by passing 3 ml of 2.5% dichloroacetic acid in dichloromethane through the column over 3.0 minutes. The orange, dimethoxytrityl cation bearing solution was reserved. The column was washed twice with 10 ml each of ACN (anhydrous).

The first coupling was accomplished by passing 10 ml more ACN (anhydrous) through the column. Then 200 μl of the G*T methylphosphoramidite was drawn into a 1 ml syringe. Next, 200 ul of 0.45M tetrazole in anhydrous ACN was likewise drawn into the syringe containing the methylphosphonamidite. The reagents were rapidly mixed in the syringe, then slowly passed through the column dropwise over 1 minute, being sure to lightly draw the plunger up and down to ensure adequate mixing with the support. After 3 minutes, 1 ml of the oxidizing reagent (0.1M $I_2$ in 74.25% THF, 25% 2,6-lutidine, and 0.25% water) was passed through the column over 1 minute. The column was then washed with 20 ml of ACN. The column was then treated for 1 minute with 600 μl of a solution containing 20% (v/v) acetic anhydride, 30% (v/v) ACN, 50% (v/v) pyridine, and 0.312% (w/v) dimethyaminopyridine. The column was washed with 20 ml of ACN.

The synthetic cycle was then repeated with each dinucleotide methylphosphonanamidite until the synthesis was completed. The order of addition of dimers after the initial G*T coupling was T*T, T*G, C*A, T*G, C*A, T*C, C*T and G*T.

The dimethoxytriyl group was removed from the oligomer at the end of the synthesis.

The oligomer was then cleaved from the support and deprotected. The support bound oligomer was removed from the synthesis cartridge and placed in a glass 1 dram vial with a screw top. The support was treated for 30 minutes at room temperature with 1 ml of a solution of acetonitrile/ethanol/ $NH_4OH$ (9/9/1). Then, 1 ml of ethylenediamine was added to the reaction vessel and the reaction allowed 6 hours to go to completion. The supernatant containing the oligomer was then removed from the support and the support was rinsed twice with 1 ml of 1/1 acetonitrile/water; the washings were combined with the supernatant. The combined solution was diluted to 30 ml total volume with water and neutralized with approximately 1.7 ml of glacial acetic acid. The neutralized solution was desalted using a Waters C-18 Sep-Pak cartridge which was pre-equilibrated with 5 ml acetonitrile, 5 ml of 50% acetonitrile/water, and 5 ml of water, sequentially. After the reaction solution was passed through the column it was washed with 5 ml of water. The product was then eluted with 2 ml of 1/1 acetonitrile/water.

The oligomer was purified by HPLC on a reverse phase column (Poros II R/E 4.6×100 mm) using a gradient of acetonitrile in water.

Example 7

Preparation of 5'-(G*A) (A*G)-(G*A)-(G*G)-(A*G)-(G*A)-(A*G) -G-3'

The grouped dinucleosides indicate the coupled dimers and the asterisks indicates where the stereochemistry is fixed (chirally defined or chirally pure) as the fast eluting dimer isomer on silica gel (identified as Rp).

This oligomer was prepared using automated synthesis coupling G*A, G*G and A*G MP(Rp)/Mp dimer synthons prepared according to the procedures of Example 1 .

An amount of G*A, G*G and A*G dimer synthons was dissolved in acetonitrile to give a concentration of 0.1M and stored over 3 Å molecular sieves (Millipore, Milford, Mass.) overnight as described in Example 6.

The dissolved dimers, with molecular sieves, were placed in conical vessels on a Millipore Expedite DNA Synthesizer which as equipped with end-line filters to remove particulites. All other reagents (oxidizer, deblock, capping reagents and activator) were prepared as described in Example 6 and applied to the appropriate positions on the instrument as instructed in the manual.

The coupling program was modified to place the oxidizing step immediately subsequent to the coupling step in order to reduce backbone cleavage prior to oxidation. (See Hogrefe, R. I., et al. "An Improved Method for the Synthesis and Deprotection of Methylphosphonate Oligonucleotides" in *Methods in Molecular Biology*, vol. 20: *Protocols for Oligonucleotides and Analogs* (ed. Agarwal, S.) pages 143–164, Humana Press, Totowa, N.Y. (1983). Table II contains the programming parameters for one synthesis cycle ("Syn4all-1 μmol")

A 1 μmole scale DNA synthesis column (Millipore) was filled with 1 μmol of methacrylate support-bound deoxyguanosine and was placed on the DNA synthesizer. The dimers were coupled sequentially from the 3' terminus. The dimethoxytrityl protecting group was removed from the oligomer at the end of the synthesis.

The oligomer was then cleaved from the support and deprotected. The support bound oligomer was removed from the synthesis cartridge and placed in a glass 1 dram vial with a screw top, The support was treated for 30 minutes at room temperature with 1 ml of a solution of acetonitrile/ethanol/ $NH_4OH$ (9/9/1). Then, 1 ml of ethylenediamine was added to the reaction vessel and the reaction allowed 6 hours to go to completion. The supernatant containing the oligomer was then removed from the support and the support rinsed twice with 1 ml of 1/1 acetonitrile/water, when combined with the supernatant. The combined solution was diluted to 50 ml total volume with water and neutralized with approximately 1.7 ml of glacial acetic acid. The neutralized solution was desalted using a Waters C-18 Sep-Pak cartridge which was pre-equilibrated with 5 ml acetonitrile, 5 ml of 50% acetonitrile/water, and 5 ml of water, sequentially. After the reaction solution was passed through the column, it was washed with 5 ml of water. The product was then eluted with 1.8 ml of 1/1 acetonitrile/water.

The crude yield was 87 $OD_{260}$ units. The Oligomers was purified on HPLC using a β-cyclobond standard phase 4.5×250 mm column (Azetec, Inc. Whippany, N.J.) with a decreasing gradient (80% to 40%) of acetonitrile in 0.05M triethylammonium acetate (pH 7). The isolated yield was 22 $OD_{260}$ units (25%). The product was characterized by electron spray mass spectrometry (calc. 5407/found 5401).

TABLE II

| Function | Mode | Amount/ Arg1 | Time (sec)/ Arg2 | Description |
| --- | --- | --- | --- | --- |
| $Deblocking | | | | |
| 144/*Advance Frac | */ NA | 1 | 0 | "Event out ON" |
| 0/*Default | */ WAIT | 0 | 1.5 | "Wait" |
| 141/*Photometer S | */ NA | 1 | 1 | "START data collection" |
| 12/*Wsh A | */ PULSE | 40 | 0 | "Wsh A" |
| 16/*Dblk | */ PULSE | 10 | 0 | "Dblk to column" |
| 16/*Dblk | */ PULSE | 200 | 120 | "Deblock" |
| 38/*Wsh A to Cl | */ PULSE | 80 | 0 | "Flush system with Wsh A" |
| 141/*Photometer S | */ NA | 0 | 1 | "STOP data collection" |
| 144/*Advance Frac | */ NA | 2 | 0 | "Event out OFF" |
| $Coupling | | | | |
| 1/*Wsh | */ PULSE | 5 | 0 | "Flush system with Wsh" |
| 2/*Act | */ PULSE | 5 | 0 | "Flush system with Act" |
| 18/*A + Act | */ PULSE | 4 | 0 | "Monomer + Act to column" |
| 18/*A + Act | */ PULSE | 4 | 45 | "Couple monomer" |
| 1/*Wsh | */ PULSE | 7 | 30 | "Couple monomer" |
| 1/*Wsh | */ PULSE | 8 | 0 | "Flush system with Wsh" |
| $Oxidizing | | | | |
| 15/*Ox | */ PULSE | 33 | 60 | "Ox to column" |
| 12/*Wsh A | */ PULSE | 15 | 0 | "Flush system with Wsh A" |

TABLE II-continued

| Function | Mode | Amount/ Arg1 | Time (sec)/ Arg2 | Description |
|---|---|---|---|---|
| $Capping | | | | |
| 12/*Wsh A | */ PULSE | 20 | 0 | "Flush system with Wsh A" |
| 13/*Caps | */ PULSE | 20 | 0 | "Caps to column" |
| 12/*Wsh A | */ PULSE | 6 | 15 | "Cap" |
| 12/*Wsh A | */ PULSE | 100 | 0 | "Flush system with Wsh A" |

Example 8

Preparation of an Oligomer Using 2'—O Methyl MP(Rp)/2'—O-Methyl MP Dimer Synthons This example describes the preparation of 5'-(C*U)-(C*U)-(C*U)-(C*U)-(C*U)-(C*U)-(C*U)-(C*U)-A-3' using 2—O methyl MP(Rp)/2'—O methyl MP dimer synthons prepared according to the methods of Example 2 hereinabove.

An amount of the appropriate dimer synthons was dissolved in acetonitrile to give concentration of 0.1M and stored over 3 Å molecular sieves as described in Example 6. Manual couplings were used with a coupling time of 2 minutes. All other reagents were prepared as described in Example 6.

A 1 μmole scale DNA synthesis column (Millipore) was filled with 1 μmole of methacrylate support bound deoxyadenosine. The dimers were coupled sequentially from the 3'-terminus. The overall coupling efficiency, based on dimethoxytrityl absorbance, was 50%, for an average of 90% per coupling. The dimethoxytrityl group was removed from the oligomner at the end of the synthesis.

The deprotection was carried out as described in Example 6. The crude yield was 25 $OD_{260}$ units.

The oligomer was purified on HPLC using a Poros II-Rp using an increasing gradient of acetonitrile in water (10% to 30% over 11 minutes. The isolated yield was 9 $OD_{260}$ units (36%). The product was characterized by electron spray mass spectrometry (calc. 4699.5/found 4701).

Alternatively the oligomer can be synthesized using an automated DNA synthesizer as follows:

The appropriate dimer synthons are dissolved in acetonitrile to give a concentration of 0.1M and stored over 3 Å molecular sieves overnight as described in Example 6. The dissolved dimer synthons, with molecular sieves, are placed in conical vessels on the Millipore Expedite DNA Synthesizer which is equipped with end-line filters to remove particulates. All other reagents (oxidizer, deblock, capping reagents and activator) are also prepared as described in Example 6 and applied to the appropriate positions on the instrument as instructed in the manual. The coupling program of Example 7 is used except that the coupling time is extended to 2 minutes.

The deprotection is carried out as described in Example 6. The oligomer can be purified on HPLC using the system described above in this Example.

Example 9

Preparation of an Oligomer Having Alternating MP(Rp)/MP(PS) Internucleosidyl Linkages The preparation of an oligomer having alternating MP(Rp)/MP(PS) internucleosidyl linkages is accomplished using dimer synthons prepared according to Example 1 and dissolved and stored over molecular sieves as described in Example 6. All parameters of synthesis, deprotation, and purification are as described in Example 7 except that the oxidizing reagent is replaced with a 0.1M solution of 3 H-1,2-benzodithiole-3-one, 1,1-dioxide ("Beaucage Reagent", See, Iyer, R. P. et al., JACS 112:1254–1255 (1990)) or a 0.1M solution of sulfur in 1/1 carbon disulfide/diisopropylethylamine.

Example 10

Preparation of an Oligomer Having 2'—O-Methyl Nucleosidyl Units and Alternating MP(Rp)/MP(PS) Internucleosidyl Linkages This oligomer is prepared using the same dimer synthons prepared according to Example 2 and described in Example 8 and following the parameters of synthesis, deprotection and purification of Example 8, except the oxidizing reagent described therein is replaced by a 0.1M solution of 3H-1, 2-benzodithiole-3-one, 1,1-dioxide or a 0.1M solution on 1/1 carbon disulfide/diisopropylamine.

Example 11

Preparation of an Oligomer Having 2'—O-Methyl Nucleosidyl Units and Alternating MP(Rp)(PS)/MP Internucleosidyl Linkages This oligomer is prepared using dimer synthons prepared according to Example 3 and by following the parameters of synthesis, deprotection and purification as described in Example 8.

Example 12

Preparation of an Oligomer Having Alternating MP(Rp)(PS)/MP Internucleosidyl Linkages This oligomer is prepared using dimer synthons as prepared according to Example 4 and by following the parameters of synthesis, deprotection and purification as described in Example 7.

Example 13

Preparation of an Oligomer Having Alternating MP(Rp)(PS)/MP(PS) Internucleosidyl Linkages This oligomer is prepared using dimer synthons prepared according to Example 4 and by following the parameters of synthesis, deprotection and purification describe in Example 7, except that the oxidizing reagent used therein is replaced by a 0.1M solution of 3H-1,2-benzodithiole, 1,1-dioxide or a 0.1M solution of sulfur in 1/1 carbon disulfide/diisopropylethylamine.

Example 14

Preparation of a MP(Rp)/MP(Rp)/MP Trimer Synthon

The above-identified trimer synthon is prepared using the dimer synthon of Example 1. The dimer methylphosphonamidite synthon is coupled to a 5'—OH, 3'-silylated nucleoside using methods analogous to those described in Example 1A for the coupling of the 3-nucleoside to the monomer phosphoramidite.

The 5'—OH, 3'-silylated nucleoside (1 equivalent) and isomerically pure Rp dimer 3'-methyl-phosphoramidite (1.25 equivalents) are weighed in to a round bottom flask and dried by coevaporation with acetonitrile. The resulting foam is dissolved in acetonitrile and treated with a solution of 0.45M tetrazole in acetonitrile (4.5 equivalents). After three minutes, the reaction product is oxidized and worked up as described in Example 1A. The diastereoisomers of the 3'-silylated trimer are resolved on a silica gel column using methods described in Example 1A for resolution of the dimer diastereoisomers. The configuration of the separated isomers is determined using 2-D nmr (ROSEY). The trimer having the desired Rp/Rp configuration is then converted to the corresponding phosphoramidite synthon by reaction with chloromethyl-N,N-diisopropylaminophosphine as described in Example 1B for the dimer synthon. Work up and purification of the trimer synthon are as described in Example 1B.

Example 15

Preparation of an Oligomer Having MP(Rp)/MP(Rp)/MP Internucleosidyl Linkage, The above-identified Oligomer is prepared using trimer synthons prepared according to Example 14 using the procedures described in either Example 6 (manual couplings) or Example 7 (automated couplings), with the trimer synthon being substituted for the dimer synthon. All other prameters of synthesis, deprotection and purification are as described in Examples 6 and 7.

Example 16

Preparation of 2'—F Dimer Synthons

Dimer synthons useful in the preparation of the oligomers of the present invention may be prepared using 2'-fluoronucleosides. Methods for preparation of 2'-fluoronucleosides have bean reported and are known to those skilled in the art. (See, e.g., Codington, JOC, Vol. 29 (1964) (2'—F U); Mangel, Angew. Chem. 96:557–558 (1978) and Doen, JOC 32:1462–1471 (1967) (2'—F C); Ikehara, Chem. Pharm. Bull. 29:1034–1038 (1981) (2'—F G); Ikehara, J. Carbohydrates, Nucleosides, Nucleotides 7:131–140 (1980) (2'—F A), and also Krug, A, Nucleosides & Nucleotides 8:1473–1483 (1989).

The preparation of dimer synthons using 2'-fluoronucleosides may be accomplishing using the procedures analogous to those described for the 2'—O-methyl dimer synthons (See, e.g., Examples 2 and 3). The resulting dimer synthons may be used to prepare oligomers using methods analogous to the methods used for the 2'—O methyl dimer synthons such as Examples 8, 10, and 11.

Example 17

Preparation of 2'—O-Allyl Dimer and Trimer Synthons and Their Use in Oligomer Synthesis The dimer and trimer synthons described in Examples 1, 4 and 14 can be prepared using 2'—O-allyl nucleosides. The preparation of 2'—O-allyl nucleosides has been reported and they are commercially available, as has been reported there use in the preparation of oligomers. (See, e.g., Iribarren, et al. (1990) Proc. Natl. Acad. Sci. (USA) 87:7747–51; and Lesnik et al. (1983), Biochemistry 32:7832–8). The nucleosides are used to prepare dimer and trimer synthons using procedures described hereinabove. The synthons are used to prepare oligomers using methods such as those described in Examples 5, 6, 7, 9, 12, 13 or 15.

Example 18

Preparation of Racemic Methylphosphonate Oligonucleotides

The oligomers were synthesized using 5'-(dimethoxytrityl) deoxynucleoside-3'-[(N,N-diisopropylamino)methyl]-phosphonoamidite monomers. Solid-phase synthesis was performed on methacrylate polymer supports with a Biosearch Model 8750 DNA synthesizer according to the manufacturer's recommendations except for the following modifications: the monomers were dissolved in acetonitrile at concentrations of 100 mM, except dG, which was dissolved in 1/1 acetonitrile/dichloromethane at 100 mM. DEBLOCK reagent=2.5% dichloroacetic acid in dichloromethane. OXIDIZER reagent=25 g/L iodine in 0.25% water, 25% 2,6-lutidine, 72.5% tetrahydrofuran. CAP A=10% acetic anhydride in acetonitrile. CAP B=0.625% N,N-dimethylaminopyridine in pyridine.

The dimethoxytriyl group was removed from the oligonucleotide at the end of the synthesis.

The oligonucleotide was then cleaved from the support and deprotected. The support bound oligonucleotide was removed from the synthesis cartridge and placed in a glass 1 dram vial with a screw top. The support was treated for 30 minutes at room temperature with 1 ml of a solution of acetonitrile/ethanol/$NH_4OH$ (9/9/1). Then, 1 ml of ethylenediamine was added to the reaction vessel and the reaction allowed 6 hours to go to completion. The supernatant containing the oligonucleotide was then removed from the support and the support rinsed twice with 2 ml of 1/1 acetonitrile/water, when combined with the supernatant. The combined solution was; diluted to 30 ml total volume with water and neutralized with approximately 4 ml of 6 N HCL. The neutralized solution was desalted using a Waters C-18 Sep-Pak cartridge which was pre-equilibrated with 10 ml acetonitrile, 10 ml of 50% acetonitrile/100 mM triethylammonium bicarbonate, and 10 ml of 25 mM triethylammonium bicarbonate, sequentially. After the reaction solution was passed through the column it was washed with 30 ml of water. The product was then eluted with 5 ml of 1/1 acetonitrile/water.

The oligonucleotide was purified by HPLC on a reverse phase column (Whatman RAC II) using a gradient of acetonitrile in 50 mM triethylammonium acetate.

Example 19

Preparation of Oligoribonucleosides

Oligoribonucleotides may be synthesized using the following procedures:

The oligoribonucleotides were synthesized using 5'—O-dimethoxytrityl-2'—O-tert-butyldimethylsilyl-3'—O-N,N-diisopropyl-β-cyanoethylphosphoramidite nucleosides (Millipore, Milford, Mass.). The syntheses were done on a 1 μmole scale with a Milligen 8750 automated DNA synthesizer using standard Milligen phosphoramidite procedures with the exception that the coupling times were extended to 12 minutes to allow adequate time for the more sterically hindered 2'—O-tert-butyldimethylsilyl RNA monomers to react. The syntheses were begun on control-pore glass bound 2'—O-tert-butyldimethylsilyl ribonucleosides purchased from Millipore. All other oligonucleotide synthesis reagents were as described in Millipore's standard protocols.

After synthesis, the oligonucleotides were handled under sterile, RNase-free conditions. Water was sterilized by overnight treatment with 0.5% diethylpyrocarbonate followed by autoclaving. All glassware was baked for at least 4 hours at 300° C.

The oligonucleotides were deprotected and cleaved from the support by first treating the support bound oligomer with 3/1 ammonium hydroxide/ethanol for 15 hours at 55° C. The supernatant, which contained the oligonucleotide, was then decanted and evaporated to dryness. The resultant residue was then treated with 0.6 mL of 1M tetrabutylammonium fluoride in tetrahydrofuran (which contained 5% or less water) for 24 hours at room temperature. The reaction was quenched by the addition of 0.6 mL of aqueous 2M triethylammonium acetate, pH 7. Desalting of the reaction mixture was accomplished by passing the solution through a Bio-Rad 10DG column using sterile water. The desalted oligonucleotide was then dried.

Purification of the oligoribonucleotides was carried out by polyacrylainide gel electrophoresis (PAGE) containing 15% 19/1 polyacrylamide/bis-acrylamide and 7M urea using standard procedures (See Maniatis, T. et al., *Molecular Cloning: A Laboratory Manual*, pages 184–185 (Cold Spring Harbor 1982)). The gels were 20 cm wide by 40 cm long and 6 mm in width. The oligoribonucleotides (60 OD Units) were dissolved in 200 μL of water containing 1.25% bromophenol blue and loaded onto the gel. The gels were run overnight at 300 V. The product bands were visualized by UV backshadowing and excised, and the product eluted with 0.5M sodium acetate overnight. The product was desalted with a Waters C18 Sep-Pak cartridge using the manufacturer supplied protocol. The product was then $^{32}$p labelled by kinasing and analyzed by PAGE.

Example 20

Hybridization of Chirally Enriched Oligomers to RNA Targets

Chirally enriched all-pyrimidine $(C^*T)_7A$ and all-purine $(A^*G)_7T$ MP-Oligomers were prepared using either Rp- or Sp-dimeric units. Control Oligomers were also prepared using the individual monomeric units. The asterisks indicate the positions of defined chirality.

Each Oligomer was annealed to a complementary synthetic RNA target and then monitored by absorbance at 260 nm as a function of temperature Sigmoidal transitions were observed corresponding to thermal denaturation of the hybridization complexes. The Tm values were determined at the midpoint of each sigmoidal transition. Previously, we have shown that $(CT)_8$ oligomer forms a double-stranded complex with RNA at neutral pH, whereas $(AG)_8$ Oligomer forms a triple-stranded complex. Thus, we anticipated that the data for each chirally enriched series would be applicable to double-stranded and triple-stranded MP/RNA helices, respectively. The Tm data is summarized below:

TABLE III

Alternating $(CT)_7$ (A)
| Oligo No. | Sequence | Configuration* |
|---|---|---|
| 2286-1 | 5'-c*t-c*t-c*t-c*t-c*t-c*t-c*t-a-3' | (Rp) |
| 2288-1 | 5'ctctctctctctct-a-3' | (R, S) |
| 2287-1 | 5'-c*t-c*t-c*t-c*t-c*t-c*t-c*t-a-3' | (Sp) |

(B)
| Oligo | Tm (1:1, RNA) | ΔTm(RNA) |
|---|---|---|
| 2286-1 | 45.5° C. | +10.4° C. |
| 2288-1 | 35.1° C. | — |
| 2287-1 | 25.4° C. | −9.7° C. |

TABLE IV

Alternating $(AG)_7$ (A)
| Oligo No. | Sequence | Configuration* |
|---|---|---|
| 2323-1 | 5'-a*g-a*g-a*g-a*g-a*g-a*g-a*g-t-3' | (Rp) |
| 2253-1 | 5'-agagagagagagag-t-3' | (R, S) |
| 2252-1 | 5'-a*g-a*g-a*g-a*g-a*g-a*g-a*g-t-3' | (Sp) |

(B)
| Oligo | Tm (1:1, RNA) | ΔTm(RNA) |
|---|---|---|
| 2323-1 | 55.2° C. | +7.2° C. |
| 2253-1 | 48.0° C. | — |
| 2252-1 | 40.0° C. | −8.0° C. |

As shown in Tables III and IV, the Rp enriched preparations have higher Tms with RNA targets. On the other hand, Sp enriched preparations have lower Tms with RNA targets.

In separate experiments, we confirmed that the chirally enriched $(C^*T)_7A$ and $(A^*G)_7T$ MP-Oligomers form double- and triple-stranded complexes with RNA at neutral pH, respectively.

These experiments described herein demonstrate that chiral enrichment can dramatically effect the binding affinities of MP-Oligomers in both a duplex and triplex motif.

Example 21

Tm Comparisons for Methylphosphonate Oligomers Containing Either Rp-Enriched or Racemic Backbones Racemic methylphosphonate oligomers and complementary RNA targets were synthesized according to the methods described in Examples 18 and 19. The MP(Rp)/MP oligomers were synthesized according to the methods described herein by coupling MP(Rp)/MP dimers. Each coupled MP(Rp)/MP dimer is indicated by parentheses in Table V below, asterisks indicate chirally pure linkages.

Annealing reaction mixtures contained equimolar amounts of methylphosphonate oligomer and RNA target oligomer (2.4 μM total strand concentration), 20 mM potassium phosphate (pH 7.2), 100 mM sodium chloride, 0.1 mM EDTA and 0.03% potassium sarkosylate. the reaction mixtures were heated to 80° C. and then slowly cooled to 4° C. over approximately 4 to 6 hours. The annealed samples were then transferred to 1 cm quartz cuvettes and absorbance at 260 nm as a function of temperature was monitored using a Varian Cary Model 3E Spectrophotometer containing a 6×6 temperature controlled sample holder and which interfaced with an IBM compatible PC computer. The temperature was varied from 50° C. to 80° C. at a ramp rate of 1° C./minute. The Tm for each melt profile is defined at the point corresponding to the first derivative (of the $A_{260}$-temperature function). Table V summarizes data obtained for a number of pairs of racemic versus Rp-enriched methylphosphonate oligomers.

Based on the observed increases in Tm, Rp-enrichment using the MP(Rp)/MP dimer coupling method described herein leads to significant enhancement in the binding energy between a methylphosphonate oligomer and its RNA target.

TABLE V

Comparison of Tm's for MP(Rp)/Mp Enriched and Racemic Methylphosphonate Oligomers

| Sequence number | Sequence | Tm | ΔTm |
|---|---|---|---|
| 2288-1 | 5'-CT-CT-CT-CT-CT-CT-CT-CT-A-3' | 34.4° C. | |
| 2286-1 | 5'-(C*T)(C*T)(C*T)(C*T)(C*T)(C*T)(C*T)-A-3' | 44.0° C. | 9.6° C. |
| 2253-1 | 5'-AGA-GAG-AGA-GAG-AG-T-3' | 48.9° C. | |
| 2323-1 | 5'-(A*G)(A*G)(A*G)(A*G)(A*G)(A*G)(A*G)-T-3' | 56.3 ° C. | 7.4° C. |
| 2517-1 | 5'-GTG-TGT-GTG-TGT-GTG-TA-3'-3-3' | 41.0° C. | |
| 2516-1 | 5'-(G*T)(G*T)(G*T)(G*T)(G*T)(G*T)(G*T)-A-3' | 48.8° C. | 7.8° C. |
| 1634-1 | 5'-TAG-CTT-CCT-TAG-CTC-CTG-3' | 38.2° C. | |
| 2570-1 | 5'-(T*A)(G*C)(T*T)(C*C)(T*T)(A*G)(C*T)(C*C)(T*C)-C-3' | 46.9° C. | 8.7° C. |
| 2688-1 | 5'-ATG-GTG-TCT-GTT-TGA-GGT-T-3' | 40.0° C. | |
| 2662-2 | 5'-(A*T)(G*G)(T*G)(T*C)(T*G)(T*T)(T*G)(T*T)(G*T)-T-3' | 47.5° C. | 7.5° C. |
| 2624-1 | 5'-GTC-TTC-CAT-GCA-TGT-TGT-C-3' | 38.6° C. | |
| 2571-1 | 5'-(G*T)(C*T)(T*C)(C*A)(T*G)(C*A)(T*G)(T*T)(G*T)-C-3' | 46.3° C. | 8.2° C. |
| 2625-1 | 5'-GCT-TCC-ATC-TTC-CTC-GTC-C-3' | 42.9° C. | |
| 2574-1 | 5'-(G*C)(T*T)(C*C)(A*T)(C*T)(T*C)(C*T)(C*G)(T*C)-C-3' | 51.8° C. | 8.9° C. |

Example 22

Inhibition of Gene Expression in a Bacterial Cell-Free Assay System

Oligomers were tested for inhibition of expression of a target sequence in a coupled transcription/translation assay bacterial system (Promega Corporation Madison, Wisconsin; Catalog #L4880). In this kit E. Coli S30 extracts and premix components supply all enzymes and reagents needed to make mRNA and protein from the CAT gene encoded by linear pBR325 DNA or the CAT gene construct containing the $(CU)_9$ triple-strand oligomer target sequence.

The cell free assay was performed according to the manufacturer's instructions, summarized as follows. In a sterile microfuge tube were mixed 40 μl premix (complete), 30 μA S30 extract for linear DNA, DNA template (1 to 5.8 μg), oligomer at various concentrations (in 50% acetonitrile/water) and water to give a total volume of 100 μl . The incubation tubes were incubated at 30° C. for 2 hours. Then 100 μl of 0.25M Tris-Hcl (pH 8.0), 0.5% bovine serum albumin, were added to each tube. The tubes were then incubated at 60° C. for 10 minutes and then centrifuged at 12K rpm in a microfuge for 5 minutes at room temperature. The supernatant (sample) was then transferred to a new tube. The sample was analyzed for inhibition immediately or stored at −20° C.

The sample reaction mixtures were analyzed for inhibition of expression using a CAT Elisa kit (5Prime3Prime, Boulder, Col.; Catalog #5307–723118). Elisa assays were performed according to the kit manufacturer's instructions and summarized as follows. Individual reaction mixtures were diluted in 1× dilution buffer. CAT standards were set up at 20, 50, 100 and 200 pg CAT per 200 μl. Then, 200 μl reaction mixture or standard were added to each CAT Elisa well. Reaction mixtures were incubated at room temperature for two hours. Plates were washed 5 times with 1× wash buffer. Then, 200 μl biotinylated antibody to CAT were added to each plate well. Plates were incubated at room temperature for 1 hour and then washed 5 times with 1× wash buffer. Then, 200μl streptavidin conjugated alkaline phosphatase was added to each well. Plates were incubated at room temperature for 30 minutes; wells were washed 5 times with 1× wash buffer. Then, 200μl color development reagent; was added to each well. Plates were incubated at 37° C. until 200 pg CAT per well standards have an $A_{405}$ equal to approximately 1.0. The $A_{405}$ of samples was read using a Molecular Device plate reader.

Two sets of oligomers (duplex and triple strand) were tested in these assays. For the first set, the mechanism of action of inhibition is [believed to be] through duplex formation with the target sequence. This first set of oligomers is targeted to the 5'-sequence of the CAT gene which includes the Shine-Dalgarno sequence (which is important for the positioning of the 30S ribosomal subunit on the mRNA). The second set of oligomers is believed to cause inhibition through formation of a triple-stranded structure at the target site. This second set of oligomers is targeted to the $(CU)_9$ sequence which has been inserted immediately downstream of the CAT AUG start site.

Data from these experiments is set forth in Tables VI and VII. For the chiral duplex-forming oligomer (2570-1), 90% inhibition was seen at 1 μM while the racemic oligomer (1634-1) showed 90% inhibition at 10 μM. Both of these oligomers showed a dose-dependent effect.

For triple-strand oligomer, the chiral oligomer (2669-1) showed approximately two times the inhibition of CAT synthesis at 1 μM relative to the racemic oligomer (2100-4) at 1 μM In both experiments, the nonspecific oligomers, both racemic and chiral, did not have a dose-dependent effect.

TABLE VI

Cell Free Transcription Translation (CFTT)
With the Chiral Wild Type CAT Oligomer
at 30° C.

| Oligomer | Concentration | % CAT Inhibition |
|---|---|---|
| 1634-1 | 10 μM | 86.6 |
| | 3 μM | 62.8 |
| | 1 μM | 40.2 |
| | 0.3 μM | 15.3 |
| | 0.1 μM | (+7.7) |
| 2570-1 | 10 μM | >92.3 (89.2*) |
| | 3 μM | >92.3 |
| | 1 μM | 86.9 |
| | 0.3 μM | 50.6 |
| | 0.1 μM | 36.4 |
| 1633-1 | 10 μM | 20.3 |
| | 1 μM | (+8.4) |
| | 0.1 μM | (+13.4) |
| 2574-1 | 10 μM | 23.0* |
| | 1 μM | 6.5 |
| | 0.1 μM | (+5.0) |

| Oligomer No. | Complementary to |
|---|---|
| 1634-1 | racemic wild type CAT |
| 2570-1 | chiral wild type CAT |
| 1633-1 | nonspecific racemic CAT (CAT 34–48) |
| 2574-1 | nonspecific oligomer |

*corrected for added ACN

TABLE VII

CFTT With the Chiral Alternating $(AG)_8$ CAT Oligmer
at 30° C.

| Oligomer | Concentration | % CAT Inhibition |
|---|---|---|
| 2100-4 | 10 μM | 95.4 |
| | 3 μM | 84.6 |
| | 1 μM | 44.1 |
| | 0.3 μM | (+2.4) |
| 2669-1 | 10 μM | 93.9 |
| | 3 μM | 92.9 |
| | 1 μM | 84.3 |
| | 0.3 μM | 36.4 |
| 2127-1 | 10 μM | 21.0 |
| | 3 μM | (+27.7) |
| | 1 μM | (+17.8) |
| | 0.3 μM | (+20.1) |

| Oligomer No. | Oligomer Sequence |
|---|---|
| 2100-4 | racemic $(A*G)_8$ |
| 2669-1 | chirally enriched $(AG)_8$ |
| 2127-1 | nonspecific racemic oligomer |

Example 23

Inhibition of Translation With Triple Helix Complex Forming Chirally Enriched Oligomers

Sequence specific inhibition of an mRNA using chirally enriched oligomers by formation of a triple helix complex was demonstrated by the following procedure.

The target sequence for the alternating chirally enriched and random racemic AG methylphosphonate 16 mer was cloned immediately 5' of the translation initiation site in the chloramphenicol acetyltransferase (CAT) gene (Gorman et al., Mol. and Cell. Bio. (1982) 2:1044–1051) in a T7 transcription vector by standard cloning techniques (Molecular Cloning, Sambrook et al. (1989) CSH Laboratory Press). Capped mRNA was transcribed with T7 polymerase (Melton, D. A. et al. (1984) Nuc. Acids Res. 12:7035–7056) and a truncated CAT mRNA that did not contain the AG target site served as an internal control, to demonstrate the specificity of this translation inhibition. Reticulocyte lysates, unlabelled amino acids, and translation buffers were obtained from Life Technologies. A mixture of ~80 ng of CAT mRNA per reaction containing the AG alternating target site (alternating stretch of CU) and ~80 ng of the internal control truncated mRNA that did not contain the AG target site per reaction along with buffers, amino acids, 35-S-Methionine (DuPont NEN, Boston, Mass.), and rabbit reticulocyte lysate were combined on ice to form the standard translation mix (Polayes, D. A., (1991) Focus 13:4). This mix was aliquoted into tubes containing the methylphosphonate Oligomers dissolved in water or 20 mM potassium acetate to give final concentrations after addition of the mix of 25 μM, 3 μM or 0.3μM. The translation reactions were allowed to proceed for 60 minutes, then 1.5 μg of RNase A was added and the reaction continued for 15 minutes. Gel loading buffer was added, and the samples were electrophoresed in 10% Acrylamide/tricine buffered pre-cast protein gels (Novex, San Diego, Calif.). The gels were fixed in 10% acetic acid 40% methanol, dried, and exposed to X-ray film for 12 to 72 hours. The proteins of the targeted CAT mRNAs containing either the alternating CU 18 nt or the random complementary CU 16 nt sites adjacent to the initiation codon were expressed at lower levels in the presence of the chirally enriched oligomer compared to the racemic oligomer. This example demonstrates that the triplex complex was able to specifically block the translation of the target gene. This inhibition is greater that the inhibition seen with unmodified DNA of similar length (Maher, L J and Dolnick, B J Nucleic Acids Res. (1988) 16:3341–3355). In each case the R form was more potent than the racemic form. This demonstrates that R chirally enriched MP Oligomers can be more potent antisense or triple strand Oligomers.

Example 24

Translation Inhibition by MP(Rp)/MP Oligomers Targeted to the Initiation Codon of mRNA in a Rabbit Reticulocyte Cell-Free System

Figure 2:
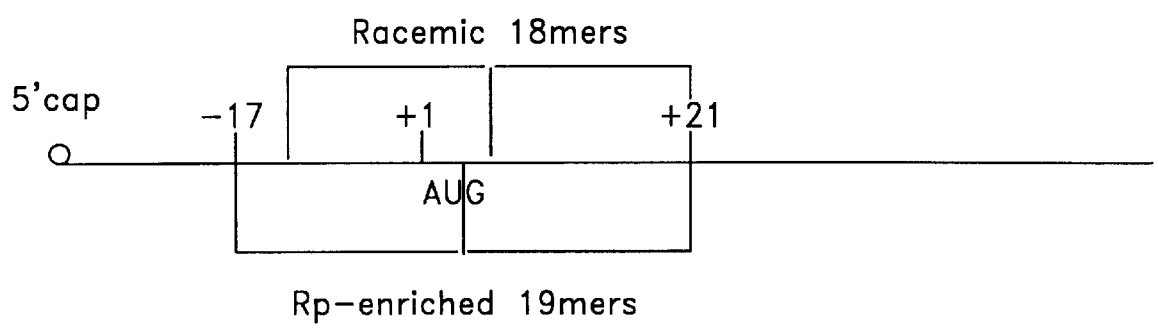
FIG. 2 depicts a schematic diagram of the CAT mRNA used in the assay of Example 24.

Inhibition of translation by tandem oligomers has been determined using a cell-free translation reaction. A schematic diagram of the CAT mRNA used in the assay and the positions of the oligomers hybridized to the mRNA are depicted in FIG. 2. Based on the convention of the adenosine of the initiation codon, AUG, being designated as the +1 position, the racemic oligomers hybridize to −5/+3 and +4 to +20. The MP(Rp)/MP Oligomers hybridized from −17/+2 and +3/+21. The oligomers were tested at concentrations of 2.0, 1.0 and 0.5 micromolar each, without any pre-annealing step. The target RNA concentration was approximately 20 nM.

The test assay was carried out according to the following procedure.

Oligomers in DEPC water (diethylpyrocarbonate-treated water) were diluted to the appropriate concentrations in eppendorf tubes to a 9 μl volume.

An RNA mix was prepared to be added to all tubes. All RNAs were capped. All RNAs were at a final concentration of about 20 μM in 10% Tris/0.1 EDTA. Two μl RNA mix was added to each reaction tube.

A translation mix was prepared containing per tube: 0.5 μl 1M potassium acetate, 0.5 μl RNAsin (Promega, Madison, Wis.) (20 units at 40 units/μl), 0.5 μl $^{35}$S-methionine at 10 μCi/μl, and 2.0 μl Translation Buffer (250 mM HEPES (pH 7.2), 400 mM KC1, 100 mM creatine phosphate, 500 μg/μl calf liver tRNA, and each of 19 amino acids (the 20 amino acids minus Met) at 500 mM each) to give 3.5 μl per reaction tube.

A 6.5 μl aliquot per tube of Rabbit Reticulocyte Lysate (Promega, Madison, Wis.) containing 3.5 mM MgCl$_2$, 0.05 mM EDTA, 25 mM KCl, 70 mM NaCl, 25 μM Hemin, 60 μg/M creatine kinase, 1 mM CaCl$_2$ and 2 mM EGTA (ethylglycol bis-beta-aminoether,N',N'-tetraacetic acid) was used.

The 3.5 μl translation mix and 6.5 μl Rabbit Reticulocyte Lysate aliquots were added to each reaction tube at 30° C. to give a final volume in each reaction tube of 21 μl. The reaction tubes were transferred to a heat block at 30° C. and incubated for an hour. To each reaction tube was added (1.5 μl RNAse A (at 1 μg/μl) (Sigma, St. Louis, Mo.) to degrade RNAs. The tubes were spun briefly to consolidate material and then incubated 15 minutes at 30° C. To each tube was added about 5 μl tricine buffer (Novex, San Diego, Calif.) with 1% β-mercaptoethanol. The tubes were heat denatured at 80° C. for 10 minutes and then allowed to cool. Samples from each tube were run on 10% acrylamide gel in tricine buffer (Novex) at 125 V, according to the manufacturer's suggested protocols. The gels were dried and used to obtain autorads overnight at −70° C. on Kodak XAR film. The gels were exposed to Bio-Rad GS-250 Molecular Imager for quantification.

Figure 3:
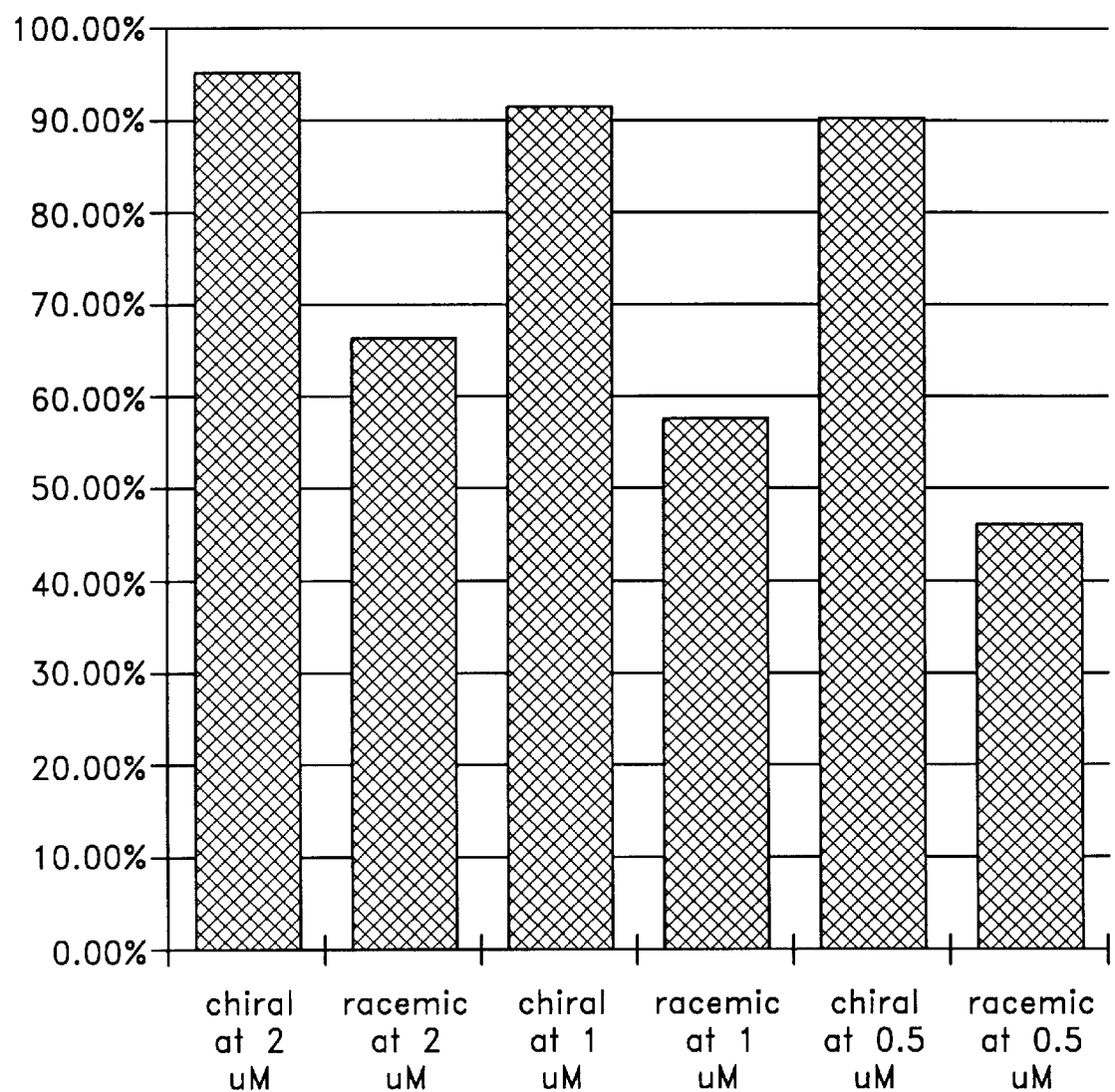
FIG. 3 depicts a bar graph showing percent inhbition of CAT translation using chirally enriched (MP(Rp)/MP) and racemic oligomers.

The percent inhibition of CAT translation using chirally enriched (MP(Rp)/MP) and racemic oligomers are reported in Table VIII and FIG. 3.

These relative percents of inhibition indicate that the chirally enriched methylphosphonate has a ten times higher affinity for the RNA target compared to the racemic methylphosphonate.

TABLE VIII

Inhibition of CAT Translation

| Oligomer | Concentration | Percent Inhibition |
|---|---|---|
| Racemic | 0.5 μM | 46.40 |
| Racemic | 1 μM | 57.94 |
| Racemic | 2 μM | 66.77 |
| MP(Rp)/MP | 0.5 μM | 90.11 |
| MP(Rp)/MP | 1 μM | 92.23 |
| MP(Rp)/MP | 2 μM | 95.51 |

We claim:

1. A method of making a Oligomer having phosphonate internucleosidyl linkages which hybridizes to an RNA target sequence said method comprising the steps of
    (a) identifying a single stranded RNA target sequence; and
    (b) synthesizing a synthetic Oligomer enriched for phosphonate internucleosidyl linkages wherein at most three out of every four adjacent linkages can have a preselected chirality and wherein the Oligomer is substantially complementary to said identified RNA target sequence.

2. A method according to claim 1 wherein greater than 40% of the phosphonate linkages are chirally pure.

3. A method according to claim 2 wherein said chirally pure phosphonate linkages are Rp lower alkylphosphonate linkages of 1 to 3 carbon atoms.

4. A method according to claim 3 wherein said Rp lower alkylphosphonate linkages are Rp methylphosphonate linkages.

5. A method of making a Oligomer which hybridizes to an RNA target sequence, said method comprising the steps of:
    (a) identifying a single stranded RNA target sequence; and
    (b) synthesizing an Oligomer having phosphonate internucleosidyl linkages selected from the group consisting of lower alkylphosphonate internucleosidyl linkages of 1 to 3 carbon atoms and lower alkylphosphonothioate internucleosidyl linkages of 1 to 3 carbon atoms wherein at least 40% of the phosphonate linkages are chirally pure, wherein at most three out of every four adjacent linkages can have a preselected chirality and wherein the oligomer is substantially complementary to said identified RNA target sequence.

6. A method according to claim 5 wherein the chirally pure phosphonate linkages are interspersed with single racemic phosphonate linkages.

7. A method according to claim 6 wherein said chirally pure phosphonate linkage are interspersed with racemic phosphonate linkages in a ratio of from 1 to about 1 to 1 to about 4 racemic phosphonate linkages to chirally pure phosphonate linkages.

8. A method according to claim 7 wherein said phosphonate linkage are lower alkylphosphonate linkages and said chirally pure linkages are Rp.

9. A method according to claim 8 wherein said lower alkylphosphonate linkages are methylphosphonate linkages.

10. A method according to claim 9 wherein the nucleosides of the oligomer have 2'—O-methyl ribosyl groups as sugar moieties.

11. A method according to claim 5 wherein said synthetic Oligomer is synthesized by linking together chirally pure Rp-configuration nucleoside dimers of the formula:

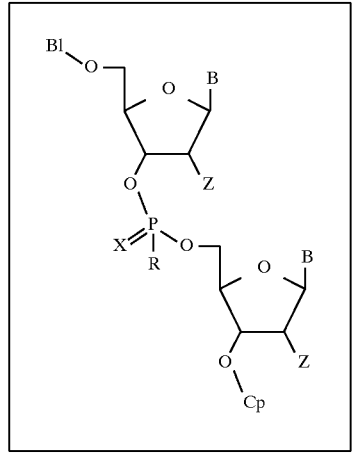

wherein X is oxygen or sulfur, R is alkyl of 1 to 3 carbon atoms, Z is hydrogen, alkoxy of from 1 to 10 carbon atoms, halogen or alkenyloxy of 3 to 6 carbon atoms; B is an optionally protected purine or pyrimidine base, B1 is a blocking group and Cp is a coupling group which when coupled to a hydroxy under coupling conditions results in a phosphonate internucleosidyl linkage.

12. A method according to claim 7 wherein X is oxygen and R is methyl.

13. A method according to claim 12 wherein the chirally pure phosphonate linkages are Rp.

14. A method according to claim 13 wherein Z is hydrogen.

15. A method according to claim 13 wherein Z is methoxy.

16. A synthetic Oligomer having enhanced potency in preventing or interfering with expression or translation of a single stranded RNA target sequence which comprises a synthetic Oligomer enriched for Rp-configuration internucleosidyl linkages selected from the group consisting of lower alkylphosphonate internucleosidyl linkages of 1 to 3 carbon atoms and lower alkylphosphonothioate internucleosidyl linkages of 1 to 3 carbon atoms wherein chirally pure phosphonate linkages are interspersed with single racemic phosphonate linkages in a ratio of from 1 to about 1 to 1 to about 4 racemic phosphonate linkages to chirally pure phosphonate linkages, wherein at most three out of every four adjacent linkages can have a preselected chirality and wherein the oligomer is complementary to the RNA target sequence.

17. An oligomer according to claim 16 wherein said phosphonate linkages are methylphosphonate linkages and said chirally pure linkages are Rp.

18. An oligomer according to claim 17 wherein the nucleosides of said oligomer have 2'—O-methyl ribosyl groups as sugar moieties.

19. A synthetic Oligomer preparation consisting of oligomers having phosphonate internucleosidyl linkages selected from the group consisting of lower alkyl phosphonate linkages wherein at most three out of every four adjacent linkages are chirally pure, of 1 to 3 carbon atoms and lower alkylphosphonothioate linkages of 1 to 3 carbon atoms wherein the oligomers have chirally pure phosphonate linkages interspersed between single racemic phosphonate linkages, wherein the oligomers are complementary to a RNA target sequence, and wherein the oligomer preparation demonstrates enhanced "net" binding affinity for the complementary RNA target sequence.

20. A method for preparing an Oligomer having a predetermined base sequence of nucleoside units and having chirally pure phosphonate internucleosidyl linkages mixed with racemic- phosphonate internucleosidyl linkages wherein the chirally pure phosphonate internucleosidyl linkages are interspersed between single racemic phosphonate internucleosidyl linkages, which method comprises linking together individual nucleoside dimers, trimers or tetramers having chirally pure phosphonate internucleosidyl linkages.

21. A method of preparing an oligomer having phosphonate internucleosidyl linkages which comprises linking together synthons having chirally pure internucleosidyl linkages of the formula:

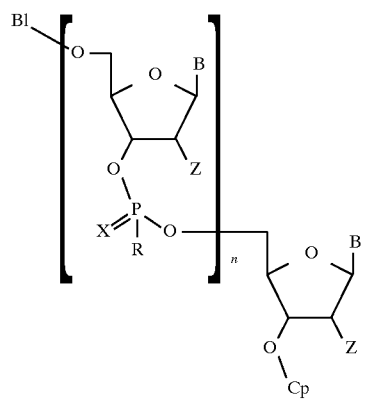

wherein X is oxygen or sulfur, R is lower alkyl of 1 to 3 carbon atoms, Z is hydrogen, alkoxy of 1 to 10 carbon atoms, halogen, or alkenyloxy of 3 to 6 carbon atoms; B is an optionally protected pyrimidine or purine base, B1 is a blocking group; Cp is a coupling group which results in a phosphonate internucleosidyl linkage when coupled to a hydroxy under coupling conditions and n is 1, 2 or 3.

22. A synthon having chirally pure phosphonate internucleosidyl linkages of the formula:

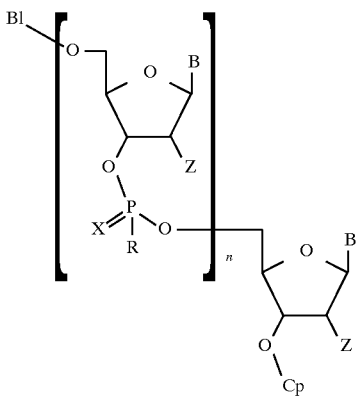

wherein X is oxygen or sulfur, R is lower alkyl of 1 to 3 carbon atoms, Z is hydrogen, alkoxy of 1 to 10 carbon atoms, halogen, or alkenyloxy of 3 to 6 carbon atoms; B is an optionally protected pyrimidine or purine base, B1 is a blocking group; Cp is a coupling group which results in a phosphonate internucleosidyl linkage when coupled to a hydroxy under coupling conditions and n is 1, 2 or 3.

* * * * *